US012765996B2

(12) United States Patent
Pham et al.

(10) Patent No.: US 12,765,996 B2
(45) Date of Patent: Oct. 20, 2026

(54) PROSTHETIC HEMI HEART VALVE

(71) Applicant: DURA LLC, Marietta, GA (US)

(72) Inventors: Thuy Pham, Marietta, GA (US); Caitlin Martin, Marietta, GA (US); Nur Hamideh, Marietta, GA (US)

(73) Assignee: SUTRA MEDICAL, INC., Lake Forest, CA (US)

( * ) Notice: Subject to any disclaimer, the term of this patent is extended or adjusted under 35 U.S.C. 154(b) by 1072 days.

(21) Appl. No.: 17/227,196

(22) Filed: Apr. 9, 2021

(65) Prior Publication Data

US 2021/0298896 A1 Sep. 30, 2021

Related U.S. Application Data

(63) Continuation-in-part of application No. 17/198,097, filed on Mar. 10, 2021, and a continuation-in-part of (Continued)

(51) Int. Cl.
*A61F 2/24* (2006.01)

(52) U.S. Cl.
CPC .......... *A61F 2/2418* (2013.01); *A61F 2/2409* (2013.01); *A61F 2230/0013* (2013.01)

(58) Field of Classification Search
CPC .................. A61F 2/2409; A61F 2/2418; A61F 2230/0013
See application file for complete search history.

(56) References Cited

U.S. PATENT DOCUMENTS

| | | | |
|---|---|---|---|
| 8,500,798 B2 | 8/2013 | Rowe et al. |
| 9,232,996 B2 | 1/2016 | Sun et al. |

(Continued)

FOREIGN PATENT DOCUMENTS

| | | |
|---|---|---|
| JP | 2005535384 | 11/2005 |
| WO | 2013040554 A1 | 3/2013 |
| WO | 2019241777 A1 | 12/2019 |

OTHER PUBLICATIONS

European Patent Office, Representative Mark Sugden, Office Action and Response for corresponding European Application No. 21784839. 9, Jan. 20, 2025, 21 pages.

(Continued)

*Primary Examiner* — Christopher D. Prone

(74) *Attorney, Agent, or Firm* — William A. English; Vista IP Law Group LLP

(57) ABSTRACT

A prosthetic hemi heart valve for treatment of a diseased heart valve having native anterior and prosthetic posterior leaflets includes a sting-ray and crescent shaped stent with an extended tab configured to be a safety mechanism. At least one prosthetic leaflet mounted on an inner surface of the stent comprises a free edge, two commissure attachment regions, an attachment edge, a coaptation region, a belly region, and at least one leg structure coupling a portion of the leaflet(s) to a lower ventricular portion of the stent. A sealing skirt coupled to the inner surface of the stent to mount the leaflet(s) and create a paravalvular seal on the atrial portion of the prosthetic hemi valve. The prosthetic hemi heart valve further having a plurality of dual guiding and fixation members for anchoring the atrial flared portion of the stent to a posterior portion of the native valve annulus.

19 Claims, 11 Drawing Sheets

Related U.S. Application Data application No. 17/121,615, filed on Dec. 14, 2020, which is a continuation of application No. PCT/US2019/037476, filed on Jun. 17, 2019, and a continuation-in-part of application No. 15/453,518, filed on Mar. 8, 2017, now Pat. No. 11,007,057.

(60) Provisional application No. 63/007,418, filed on Apr. 9, 2020, provisional application No. 62/988,253, filed on Mar. 11, 2020, provisional application No. 62/685,378, filed on Jun. 15, 2018, provisional application No. 62/427,551, filed on Nov. 29, 2016, provisional application No. 62/413,693, filed on Oct. 27, 2016, provisional application No. 62/305,204, filed on Mar. 8, 2016.

(56) References Cited

U.S. PATENT DOCUMENTS 11,007,057 B2 5/2021 Pham et al.
2003/0199975 A1* 10/2003 Gabbay .................. A61F 2/2454 623/1.14
2004/0236419 A1* 11/2004 Milo .................. A61B 17/0644 606/155
2014/0052237 A1 2/2014 Lane et al.
2014/0067048 A1* 3/2014 Chau ..................... A61F 2/2412 623/2.1
2020/0229918 A1 7/2020 Pham et al.
2021/0212824 A1 7/2021 Pham et al.
2021/0212825 A1 7/2021 Pham et al.

OTHER PUBLICATIONS

Japanese Patent Office, Hiroshi, Office Action and Response for corresponding Japanese Application No. 2022-560890, 16 pages.
Korean Intellectual Property Office, International Search Report for corresponding International Application No. PCT/US2021/026710, Jul. 28, 2021, 5 pages.
Korean Intellectual Property Office, Written Opinion for corresponding International Application No. PCT/ US2021/026710, Jul. 28, 2021, 9 pages.

* cited by examiner

PROSTHETIC HEMI HEART VALVE

CROSS REFERENCE TO RELATED APPLICATIONS

The present application claims benefit of U.S. provisional application Ser. No. 63/007,418, filed Apr. 9, 2020, and is a continuation-in-part of application Ser. No. 15/453,518, filed Mar. 8, 2017, now U.S. Pat. No. 11,007,057, which claims the benefit of U.S. provisional application Ser. No. 62/305,204, filed Mar. 8, 2016, 62/413,693, filed Oct. 27, 2016, and 62/427,551, filed Nov. 29, 2016, and is a continuation-in-part of co-pending application Ser. No. 17/121,615, filed Dec. 14, 2020, which is a continuation of International application No. PCT/US2019/037476, filed Jun. 17, 2019, which claims benefit of U.S. provisional application Ser. No. 62/685,378, filed Jun. 15, 2018, and is a continuation-in-part of co-pending application Ser. No. 17/198,097, filed Mar. 10, 2021, which claims benefit of U.S. provisional application Ser. No. 62/988,253, filed Mar. 11, 2020; the disclosures of which, including specification and drawings, are all expressly incorporated herein in their entirety by reference.

STATEMENT REGARDING FEDERALLY SPONSORED RESEARCH AND DEVELOPMENT

This invention was made with Government support under Contract R44 HL140835 awarded by the National Institutes of Health. The Government has certain rights in the invention.

FIELD OF THE INVENTION

The application relates generally to replacement heart valves, e.g., for replacing diseased mitral and/or tricuspid valves. More particularly, embodiments of the subject matter relate to tissue-based, collapsible and expandable replacement heart valves.

BACKGROUND

The mitral valve (MV) has two distinct large leaflet cusps, or leaflets. As shown in FIG. 1A, the MV is on the left side of the heart and located between the left atrium and the left ventricle. The mitral valve apparatus consists of a mitral annulus, two leaflets, chordae tendineae ("chords"), two papillary muscles and the left ventricular myocardium. Referring to FIG. 1B, the mitral annulus is subdivided into an anterior portion and a posterior portion. Normally, the anterior mitral leaflet (AML) is connected to the aortic valve via the aortic-mitral curtain, and the posterior mitral leaflet (P-L) is hinged on the posterior mitral annulus. The chords originate from either the two major papillary muscles or from multiple small muscle bundles attaching to the ventricular wall and connect to the free edge of the mitral leaflets. Chords are composed mainly of collagen bundles, which give the chords high stiffness and maintain minimal extension to prevent the leaflets from billowing into the left atrium during systole.

When the mitral valve is closed, the respective anterior and posterior leaflets are in close contact to form a single zone of apposition. As one skilled in the art will appreciate, normal mitral valve function involves a proper force balance, with each of its components working congruently during a cardiac cycle. Pathological alterations affecting any of the components of the mitral valve, such as chord rupture, annulus dilatation, papillary muscle displacement, leaflet calcification, and myxomatous disease, can lead to altered mitral valve function and cause mitral valve regurgitation (MR).

Mitral regurgitation is dysfunction of the mitral valve that causes an abnormal leakage of blood from the left ventricle back into the left atrium during systole (i.e., the expulsion phase of the heart cycle in which blood moves from the left ventricle into the aorta). While trivial mitral regurgitation can be present in healthy patients, moderate to severe mitral regurgitation is one of the most prevalent forms of heart valve disease. The most common causes of mitral regurgitation include ischemic heart diseases, non-ischemic heart diseases, and valve degeneration. Both ischemic (mainly due to coronary artery diseases) and non-ischemic (idiopathic dilated cardiomyopathy for example) heart diseases can cause functional, or secondary, mitral regurgitation through various mechanisms, including impaired left ventricle wall motion, left ventricle dilatation, and papillary muscle displacement and dysfunction. In functional mitral regurgitation, the mitral valve apparatus remains normal. Incomplete coaptation of the leaflets is due to enlargement of the mitral annulus secondary to left ventricle dilation and possibly left atrium enlargement. In addition, patients with functional mitral regurgitation can exhibit papillary muscle displacement due to the left ventricle enlargement, which results in excessive tethering of the leaflets. In contrast, degenerative (or organic) mitral regurgitation is caused by structural abnormalities of the mitral leaflets and/or the subvalvular apparatus, which can include stretching or rupture of tendinous chords.

The current treatments for mitral valve diseases include surgical repair and replacement of the mitral valve. Mitral valve repair, benefiting from improved understanding of mitral valve mechanics and function, may be now preferred to complete mitral valve replacement. However, the complex physiology and three-dimensional anatomy of the mitral valve and its surrounding structure present substantial challenges when performing these repair procedures.

In one early example of a transcatheter mitral valve replacement device, Endovalve-Herrmann (Micro Interventional Devices, Inc.), developed a mitral prosthesis that had a foldable Nitinol-based valve with a sealing skirt. Similarly, Tendyne Holdings, Inc. produces a prosthetic mitral valve replacement device comprising a pericardial valve with a self-expandable Nitinol stent. The device is designed for transapical delivery and has a ventricular fixing anchor. CardiAQ uses a pericardial valve with a Nitinol self-expandable stent in their mitral valve replacement device. Finally, Tiara (Neovasc, Inc.) uses a mitral valve replacement system that is deliverable trans-apically with a 30 Fr catheter that has anchor structures, and a pericardial valve on a self-expandable stent with a D-shaped atrial portion and a ventricular portion that has an outer coating. These devices and the techniques to deliver the mitral prosthesis into the operative position are still at development stages and, though promising, challenges to the efficacy of these devices continue to exist.

The noted challenges to an efficacious mitral valve replacement device generally include operative delivery challenges; positioning and fixation challenges; seal and paravalvular leakage challenges; and hemodynamic function challenges such as left ventricular outflow tract (LVOT) obstruction. With respect to the noted operative delivery challenges, since a conventional mitral prosthesis is larger than a conventional aortic prosthesis, it is more difficult to fold and compress the larger mitral prosthesis into a catheter for deployment as well as retrieval through either conventional trans-apical or trans-femoral delivery techniques.

Turning to the positioning and fixation challenges, instability and migration are the most prominent obstacles given that the mitral valve is subjected to high and repetitive loads in a cardiac cycle, with a high transvalvular pressure gradient that is near zero at diastole and can rise to 120 mmHg or more during systole and higher than 150 mmHg of systolic pressure for patients with aortic stenosis and systemic hypertension. The lack of calcium distribution at the mitral annulus also affects device stability and anchoring. Further, the transcatheter mitral valve replacement can be easily dislodged as the heart moves during each beating cycle.

With respect to sealing and paravalvular leakage, a good fit between the native annulus and the prosthesis that minimizes paravalvular leak is desirable. Since the mitral valve annulus is large, typically, a prosthetic mitral valve may have a large overhanging atrial portion or flare which can prevent leakage, but, problematically, it also requires a large valve size at the ventricular level so that the prosthesis can be tightly fitted in the native mitral valve. Conventionally, a prosthetic mitral valve is smaller than the diseased native valve and additional material is added around the prosthetic valve to compensate for the large native mitral annulus. Undesirably, adding more material to a prosthetic valve increases the size of the delivery system.

Finally, with respect to the preservation of hemodynamic function, the operative positioning of a prosthetic mitral valve, which is conventionally large as described above, should not obstruct the LVOT at the anterior portion of the mitral annulus and should not interfere with the associated structures of a native mitral valve.

Accordingly, it would be beneficial to have a heart valve leaflet replacement system that does not suffer from the shortcomings and deficiencies of conventional valve prosthetics. It is desirable to secure the prosthetic mitral valve replacement system to the native mitral annulus. It is also desirable to improve positioning of a mitral prosthesis and prevent leaking of blood between the mitral prosthesis and the native mitral valve. Similarly, it is desirable to prevent further dilation of the native mitral annulus. Furthermore, other desirable features and characteristics will become apparent from the subsequent detailed description and the appended claims, taken in conjunction with the accompanying drawings and the foregoing technical field and background.

SUMMARY

Described herein are examples of a prosthetic hemi heart valve or prosthetic hemi-valve and a method of securing a prosthetic hemi-valve to one of the native valve annuli. It is contemplated that the method of securing a prosthetic hemi-valve to one of the native valve annuli is configured to prevent dislodgement of the prosthetic hemi-valve from the annulus and to ensure the proper coaptation between the implanted prosthetic hemi-valve leaflets with the remaining native leaflets. It is contemplated that the prosthetic hemi-valve can be implanted via an open surgical procedure or percutaneously via catheter. In one aspect, the prosthetic hemi-valve comprises a plurality of dual guiding and fixation (DGF) members, described elsewhere herein, which can be configured to secure the prosthetic hemi-valve to the native mitral annulus. In a further aspect, the associated methods can be configured to implant the replacement valve prosthesis and to help prevent further dilation of the native mitral annulus. For clarity, it will be appreciated, although the present disclosure may focus on the treatment of functional mitral regurgitation, it is contemplated that the heart valve leaflet replacement system and the associated methods can be used or otherwise configured to be used to treat other valve disease conditions such as degenerative mitral regurgitation and replace other valves (e.g., tricuspid valve) of the human heart, or could be used or otherwise configured to be used in other mammals suffering from valve deficiencies as well.

In one aspect, the prosthetic hemi-valve is configurable or otherwise sizable to be crimped down to fit within a delivery sheath and to subsequently be selectively re-expanded to an operative size and position once removed from the delivery sheath within the heart. In a further aspect, at least a portion of the prosthetic hemi-valve can have a stent shape, which can comprise an upper atrial portion and a lower ventricular portion. In one aspect, the atrial portion can be configured to facilitate anchoring of the stent, which can help prevent paravalvular leakage and dislodgement of the stent. Further, the ventricular portion can displace a diseased native leaflet out of the blood flow tract and house at least one prosthetic leaflet. In another aspect, the prosthetic hemi-valve can comprise a lining skirt that can be coupled to at least a portion of the inner and/or outer surfaces of the stent. In one exemplary aspect, at least one prosthetic leaflet can be mounted on the inner lumen of the stent and/or on at least a portion of the outer side of the stent, which can function in place of at least one native leaflet to restore normal valve function, i.e., to prevent mitral regurgitation.

In one aspect, at least one prosthetic leaflet of the prosthetic hemi-valve can be configured with at least one leg structure which prevents the valve leaflet from billowing into the atrium and prolapsing. The at least one leg structure also acts to distribute prosthetic leaflet stress and facilitate the coaptation with at least one of the native mitral valve leaflets, in order to recreate the competent closure anatomy of a native mitral valve with sufficient leaflet coaptation length and height and proper leaflet angles during systole.

In one aspect, the delivery of the prosthetic hemi-valve can be conducted using several desired delivery access approaches, such as, for example and not meant to be limiting, a surgical approach, a trans-septal approach, a trans-atrial, or a trans-apical approach, similar to the methods disclosed in the applications incorporated by reference herein. In one exemplary aspect, the trans-septal approach can comprise creating an opening in the internal jugular or femoral vein for the subsequent minimally invasive delivery of portions of the prosthetic hemi-valve through the superior vena cava, which flows into the right atrium of the heart. In this exemplary aspect, the access path of the trans-septal approach crosses the atrial septum of the heart, and once achieved, the components of the prosthetic hemi-valve can operatively be positioned in the left atrium, the native mitral valve, and the left ventricle. In one aspect, it is contemplated that a main delivery catheter can be placed along the access path to allow desired components of the prosthetic hemi-valve to be operatively positioned in the left atrium without complications.

In one aspect the prosthetic hemi-valve has a unique crescent-shape, forming a half- or hemi-valve. The prosthetic hemi-valve is configured to have a ventricular portion that lies in the left ventricle and displaces at least one diseased native mitral leaflet. An atrial portion of the hemi-valve is configured to prevent paravalvular leak and engage with DGF members to fix the entirety of the prosthetic hemi-valve on the mitral annulus. An angled neck region forms a transition between the ventricular and atrial portions of the hemi-valve.

In an additional aspect, the stent is configured to span at least a portion, or the entirety, of the circumference of the native posterior mitral valve via a network of compressible and self-expanding diamond-shaped cells occupying a non-uniform, semi-elliptical shape with varying lengths as to avoid interfering with surrounding native valve structures. In a further aspect, the stent can assume an asymmetric, semi-conical or semi-circular cross-sectional profile.

In one aspect, the atrial portion of the stent includes a plurality of cells that assume a shape designed to conform to the native mitral annulus. The atrial portion of the stent includes curved atrial stent tips so as to not interfere with the atrial wall, and a plurality of through-holes. It connects to the neck region that curves downward along the native mitral annulus and transitions to the ventricular portion of the stent.

In a further aspect, the through-holes on the atrial portion of the stent are configured to accept DGF locking members to fix the prosthetic hemi-valve in place on the mitral annulus.

In one aspect, the neck region transitions from the atrial portion to the ventricular portion of the stent. The ventricular portion of the stent is configured with at least one prosthetic leaflet coupled to the inner surface, which is configured to form a C-shape which can extend to a D-shape in systole in the operative position.

In one aspect, the ventricular portion of the stent can be configured with a plurality of through-holes to facilitate attachment of at least a portion of the prosthetic leaflet.

In one aspect, a plurality of tabs extends from the ventricular portion of the stent, e.g., making the stent a shape similar to a stingray. The tabs can be directly extended from the tips of the stent, or coupled via an extended strut. The tabs are configured to be a safety mechanism for the prosthetic valve throughout the housing, positioning, and locking process.

In one aspect, a component of the prosthetic hemi-valve is at least one dome-shaped prosthetic leaflet. At least one prosthetic leaflet can be mounted to the inner surface of the ventricular portion of the stent frame, and displace at least one diseased native posterior mitral leaflet.

In an operative aspect, the prosthetic valve includes a plurality of dome-shaped leaflets, which are configured to be flexible and mobile throughout the cardiac cycle. During the systolic phase, the at least one prosthetic leaflet extends radially to form a D-shape to coapt with healthy native anterior leaflets by extending radially outwards from the stent, thus preventing transvalvular leakage and mitral regurgitation. During diastole, the at least one prosthetic leaflet is configured to move towards the stent in a C-shape to allow for ventricular filling.

Due to the hemi-valve nature of the device, it is contemplated that thicker leaflet material can be used to enhance prosthetic valve durability. Furthermore, the half-valve can also be crimped to a smaller profile, compared to a full-valve, allowing a greater portion of the at-risk population to undergo a transcatheter mitral valve replacement operation.

In an exemplary embodiment, the at least one prosthetic leaflet can mimic the configuration of the native mitral posterior leaflets with three adjoined semilunar cusps extended from the neck portion of the stent into the ventricle, with the central cusp extending further downwards and radially inwards than the two smaller lateral cusps. In a further embodiment, each prosthetic leaflet can comprise a parabolic attachment line, two commissures, a belly region, a coaptation region and optionally, at least one leg.

In one embodiment, the central leaflet attachment line is configured to be symmetrical about the axial midline, with the central prosthetic leaflet spanning one-third to two-thirds of the ventricular portion of the stent. The two lateral leaflets are configured to mirror each other on either side of the central leaflet, spanning one-sixth to one-third of the ventricular portion of the stent, and are asymmetric about their respective axial midlines.

In an exemplary aspect, the prosthetic valve includes a plurality of prosthetic leaflets, which are configured to have arm structures extending from the commissures that stabilize the commissure region of the prosthetic leaflets by restricting backwards motion of the prosthetic leaflet towards the stent frame during the diastolic phase of the cardiac cycle.

In one aspect, the arm structures can be configured to fold-over portions of the at least one prosthetic leaflet to increase the leaflet thickness at the commissure region. It is contemplated that, in exemplary embodiments, the arm structures can be triangular, rectangular, or irregularly shaped.

In a further aspect, at least one dog-bone, rectangular, cylindrical-, or conical shaped leg structure may be provided on the prosthetic leaflet, which can be configured to attach to, and extend radially away from, the stent frame. One skilled in the art can appreciate that the leg structures mimic the native chordae tendineae, in that they can prevent over-extension and prolapse of the prosthetic leaflet, which is especially necessary with larger prosthetic leaflets. The leg structures also serve to distribute force throughout the prosthetic leaflet and frame.

In one embodiment, the prosthetic hemi-valve is configured to occupy about one-half of the mitral orifice in the D-shape configuration when coapting with the native anterior mitral leaflets. The prosthetic leaflets are designed to extend radially inwards, up to the lateral edges of the stent, and not beyond.

In one aspect, a skirt is coupled to at least a portion of the inner and outer surface of the stent. The skirt serves dual purposes: acting as a means to mount the prosthetic leaflets onto the ventricular portion of the stent, and also creating a paravalvular seal along the atrial portion of the stent.

In one aspect, the skirt material can be made of polymers, fabric, biological tissue, and the like. An important characteristic of the skirt is that it is biaxially oriented, allowing it to stretch in both the axial and transverse direction during crimping and expansion of the prosthetic hemi-valve.

In one aspect, the skirt can be a single piece of material, or alternatively, the skirt can be configured from multiple separate pieces of material, coupled to the stent via one or more non-absorbable sutures or strings.

In one embodiment, a sealing ring can be coupled to the circumference of the prosthetic hemi-valve to promote tissue ingrowth, and to protect the native mitral valve surrounding structures from abrasion by the prosthetic valve.

In one aspect, a plurality of DGF members can be operatively positioned and implanted at desired locations in the native annulus prior to the delivery of the replacement prosthetic hemi-valve. In this aspect, the DGF members can improve the subsequent positioning and anchoring of the replacement prosthetic hemi-valve. In a further aspect, the plurality of DGF members can help prevent leakage of blood between the operatively positioned prosthesis and the native mitral valve.

In an exemplary aspect, the DGF members can comprise a permanent head and body portion with a removable flexible tail portion. The DGF head member can comprise a coil shape that can be operatively embedded in the annular tissue. The DGF body member can be coupled to a plurality of DGF locking members to fix the prosthetic hemi-valve device onto the native mitral annulus. The DGF tail member can be configured as a tether component that extends from the proximal portion of the DGF body, and links the DGF member to the crimped prosthetic hemi-valve within the prosthetic hemi-valve delivery and implantation system.

In one aspect, the DGF member body is coupled to a plurality of DGF locking members. In one embodiment, the DGF locking members comprise a plurality of radially compressible legs, e.g., forming a cone shape. In a further embodiment, the tip of the cone is configured to have a smaller diameter than the legs of the cone, and also a diameter smaller than the holes on the atrial portion of the stent, while the legs of the cone have a larger diameter than the holes on the atrial portion of the stent.

In one embodiment, the DGF tails can be tensioned to pull the DGF locking members through the holes on the atrial portion of the stent, thereby compressing the legs of the DGF locking members inward to allow for the passage of the DGF locking member through the hole of the atrial portion if the stent. After passing through the holes in the atrial portion of the stent, the legs of the DGF locking members re-expand to their operative position, and prevent backward motion of the DGF locking member through the holes in the atrial flare portion of the stent, effectively locking the prosthetic hemi-valve in the operative position.

Various implementations described in the present disclosure can include additional systems, methods, features, and advantages, which can not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

A better understanding of the features and advantages of the present subject matter will be obtained by reference to the following detailed description that sets forth illustrative embodiments and the accompanying drawings. The features and components of the following figures are illustrated to emphasize the general principles of the present disclosure. Corresponding features and components throughout the figures can be designated by matching reference characters for the sake of consistency and clarity.

FIG. 1A shows that the mitral leaflets coapt to form a “fish-mouth” coaptation line.

DETAILED DESCRIPTION OF THE EXEMPLARY EMBODIMENTS

Figure 1A:
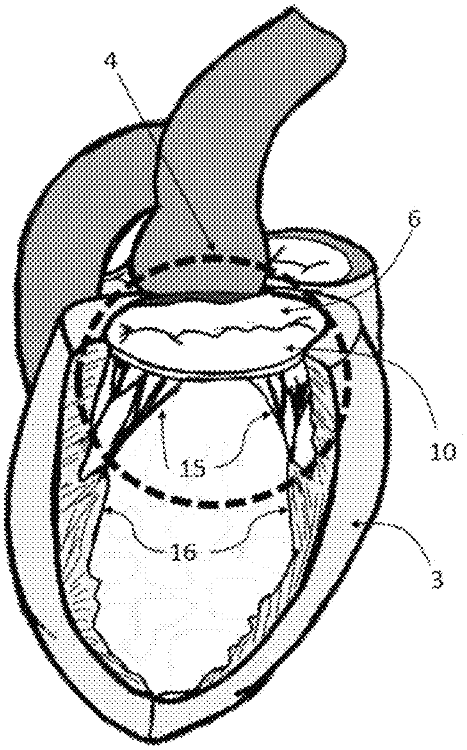
FIG. 1A is a prospective posterior cross-sectional view of the healthy native mitral valve during systole.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of embodiments described herein without utilizing other features.

Accordingly, those who work in the art will recognize that many modifications and adaptations are possible and can even be desirable in certain circumstances and are a part of the present invention. Thus, the following description is provided as illustrative of the principles of the present invention and not in limitation thereof.

For clarity, it will be appreciated that this disclosure will focus on the treatment of functional mitral regurgitation, however it is contemplated that the heart valve leaflet replacement system and the associated methods can be used or otherwise configured to be used to treat other types of mitral regurgitation or to replace other diseased valves of the human heart, such as tricuspid valve, or could be used or otherwise configured to be used in other mammals suffering from valve deficiencies as well.

As used throughout, the singular forms “a,” “an,” and “the” include plural referents unless the context clearly dictates otherwise. Thus, for example, reference to “a leaflet” can include two or more such leaflets unless the context indicates otherwise.

Ranges can be expressed herein as from “about” one particular value, and/or to “about” another particular value. When such a range is expressed, another aspect includes from the one particular value and/or to the other particular value. Similarly, when values are expressed as approximations, by use of the antecedent “about,” it will be understood that the particular value forms another aspect. It will be further understood that the endpoints of each of the ranges are significant both in relation to the other endpoint, and independently of the other endpoint.

As used herein, the terms “optional” or “optionally” mean that the subsequently described event or circumstance can or cannot occur, and that the description includes instances where said event or circumstance occurs and instances where it does not.

The word “or” as used herein means any one member of a particular list and also includes any combination of members of that list. Further, one should note that conditional language, such as, among others, “can,” “could,” “might,” or “may,” unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular embodiment.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these cannot be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of the exemplary embodiments.

Throughout the description, the terms “prosthetic valve” and “prosthesis” and “valve stent” and “heart valve leaflet replacement device” and “valve device” are used interchangeably and is contemplated as a heart valve replacement device described herein.

Figure 2A:
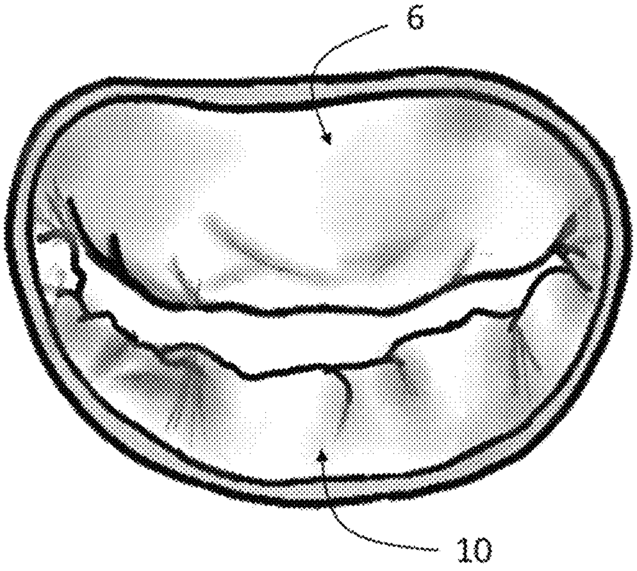
FIG. 2A illustrates the native mitral valve from an atrial view. It is clear that the native anterior leaflet is larger than the native posterior leaflet. The native posterior leaflet forms a C-shape along the posterior annulus.

Referring to FIG. 1A, the mitral valve leaflets consist of anterior 6 and posterior 10 leaflets, originating from the annulus and extending into the left ventricle 3. In a healthy patient, the anterior mitral leaflet 6 and the posterior mitral leaflet 10 come together and coapt during systole to prevent backward flow through the mitral valve 4. The posterior mitral leaflet 10 forms a “C-shape” extending from the posterior annulus, as shown in FIG. 2A. In a diseased state, the posterior leaflet 10 may not fully coapt with the anterior leaflet 6 due to posterior leaflet 10 tethering and/or dilation of the mitral annulus leading to mitral regurgitation.

Figure 2B:
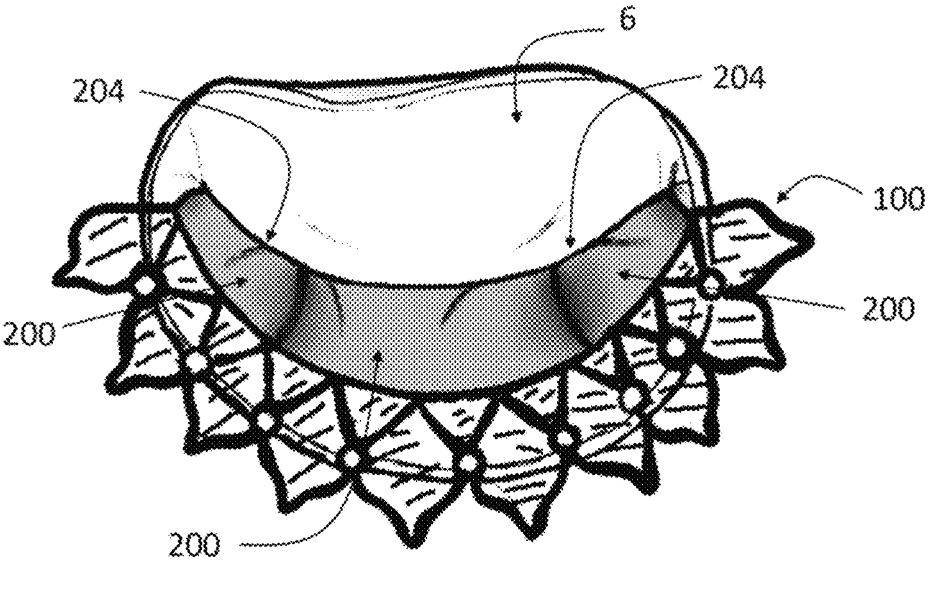
FIG. 2B is a schematic view of an exemplary aspect of a prosthetic hemi-valve device including three prosthetic leaflets mounted on the inner surface of the frame in operation at a pressurized, systolic state. The prosthetic P1, prosthetic P2, and prosthetic P3 are shown coapting with the native anterior mitral leaflet.

Turning to the drawings, an exemplary embodiment of a prosthetic hemi-valve device 1 is shown that is designed to treat mitral regurgitation in patients with regurgitation and normal anterior mitral leaflet 6 motion by replacing the posterior mitral leaflet 10, e.g., as shown in FIG. 2B. The prosthetic hemi-valve device 1 comprises a crescent-shaped frame or stent 100 which is secured to the posterior mitral annulus and positions at least one prosthetic leaflet 200 over the native posterior leaflet 10 such that it forms a coaptation region 204 with the native anterior mitral leaflet 6 during systole in operation. In this aspect, the prosthetic leaflet(s) 200 extend from the stent 100 to form a C-shape similar to the native posterior leaflet 10, but notably, they can extend further radially so as to coapt with the native anterior mitral valve 10 in dilated hearts.

In one exemplary aspect, the prosthetic hemi-valve device 1 can include a crescent-shaped stent 100, at least one dome-shaped prosthetic leaflet 200, and at least one sealing skirt 300 to facilitate sealing and mounting of the prosthetic leaflet 200 onto the stent 100. The prosthetic hemi-valve device 1 is configured such that at least one prosthetic leaflet 200 will coapt with at least one native anterior leaflet 6 during the systolic phase of the cardiac cycle in operation, e.g., as shown in FIG. 2B.

In one aspect, it is contemplated that, in the expanded configuration, the stent 100 can define a substantially semi-circular cross-sectional profile. It is further contemplated that the stent 100 can be configured such that the surface of the stent 100 defines a non-circular cross-sectional profile, including but not limited to, a semi-elliptical cross-sectional profile or an asymmetric cross-sectional profile, e.g., to at least partially conform to the shape of the natural valve annulus. As used herein, the term “asymmetric cross-sectional profile” includes any non-circular cross-sectional shape.

Figure 3A:
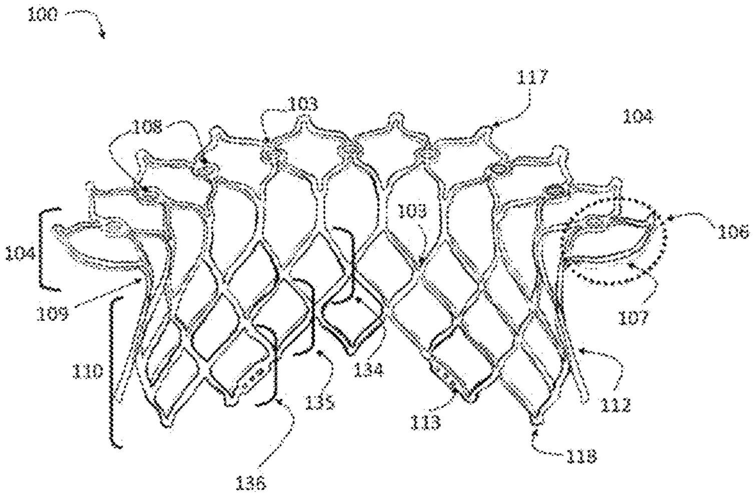
FIG. 3A is a schematic front view of an exemplary embodiment of a prosthetic hemi-valve frame including a plurality of cells, which may be included in a prosthetic hemi-valve, such as that shown in FIG. 2B. The frame comprises an upper atrial portion and a lower ventricular portion which are separated by a neck region. The atrial portion of the frame has a plurality of through-holes and curved stent-tips. The lower ventricular portion is configured with a plurality of through-holes for attachment of a prosthetic leaflet, and a variable stent height along its circumference.

In one aspect, referring to FIG. 3A, the stent 100 is configured with a crescent shape to form a half- or hemi-valve. In this aspect, the stent 100 can have a hemi-conical shape. The hemi-conical stent 100 includes an upper atrial portion 104, a lower ventricular portion 110, and a neck region 109 between the upper atrial 104 and the lower ventricular 110 portions, thereby defining a longitudinal axis therebetween, i.e., aligned along the length of the stent 100.

Referring again to FIG. 3A, the stent 100 of the hemi-valve can be made from a self-expanding or balloon-expandable material formed into a network of cells or a mesh. In this aspect, the stent frame 100 can be laser cut or woven from deformable, biocompatible materials, such as stainless steel or cobalt chromium for balloon-expandable devices, or Nitinol for self-expandable devices with memory-shape properties. In a further aspect, the stent 100 can be configured to be collapsible, crimped and expanded into the desired loading and operative positions, respectively.

In one aspect, the atrial portion 104 of the stent can be configured to be positioned on or above the native mitral annulus to facilitate anchoring and sealing of the prosthetic hemi-valve 1.

In addition or alternatively, the atrial portion 104 of the stent may be configured to span at least some or all of the native mitral annulus.

In one aspect, the atrial portion 104 of the stent is configured to flare out radially over some or all of the posterior annulus of the native mitral annulus. In this aspect, the upper atrial portion 104 can be configured with at least one row of cells. In the example shown, the cells include struts that are oriented in a collapsible diamond-shaped structure that extend outward radially from the neck portion 109 of the stent. In this aspect, the diameter of the upper atrial portion 104 is smallest near the neck portion 109 and increases moving outward towards the atrial crowns 117 and the left atrial wall.

Referring to FIG. 3A, the atrial portion 104 of the stent is configured with compressible cells. In one aspect, the atrial portion 104 of the stent comprises at least one row of cells. The cells include a collapsible network of struts that are oriented in a diamond-shaped configuration that extend outward radially from the neck portion 109 of the stent. The height of the cells can be between approximately six and twelve millimeters (6-12 mm) in height. In the example shown, each cell is formed with four struts, two upper and two lower struts. The dimensions of the upper and lower struts can be the same or different. The upper and lower struts are joined together by a cell bridge, referred to as a junction 103. The junctions 103 can be designed to be either compressible or non-compressible with the entire stent 100.

In an exemplary aspect, some of the junctions 103 of the atrial portion of the stent can be configured with a through-hole or hole 108. In this aspect, the through-holes 108 are used for anchoring and fixing the stent 100 onto the mitral annulus. The holes 108 can be configured with an inner diameter of approximately 0.5 to three millimeters (0.5-3 mm), and approximately five to fifteen (5-15) holes can be configured along the atrial portion 104 of the stent. The holes 108 in the atrial portion 104 of the stent are configured to allow for passage of the locking members 131 in one direction only.

In another aspect, the fixation of the stent 100 to the mitral annulus can be also achieved by other methods such as one or more of using adhesives, tissue grabbing, capturing, and suturing methods.

In an optional aspect, the holes 108 can have circular, rectangular, square or oval shapes.

In one aspect, because of the hemi aspect of the prosthetic valve 1, lateral edge 107 of the lateral cells 106 of the atrial portion 104 of the stent do not share a junction 103 with adjacent cells.

In this aspect, the junction 103 of the lateral cells 106 can be configured with binding sites on the lateral edges 107. In this aspect, the binding sites of the lateral edges 107 of the stent can be configured with matching corresponding shapes such that they fit together snugly and keep the stent in a cylindrical configuration throughout crimping. In this aspect, the shape of one junction 103 on one side can be configured to match and fit to the shape of the other junction on the opposite side.

In one exemplary aspect, the binding sites can be straight, zigzagged, wavy, semi-circular, semi-oval, rectangular or irregular shaped struts.

In one aspect, the atrial portion 104 of the stent is configured to conform to the annulus in operation. The upper struts of the cells on the atrial portion 104 of the stent, also referred to as crowns or free stent tips, can be configured with curved tips 117, e.g., as shown in FIG. 3A, so as not to interfere with the left atrial wall 2 in operation. In an exemplary embodiment, the curved angle of the tips 117 can be approximately 90°-145° with respect to the rest of the upper flare portion 104. Such a curvature allows the atrial portion 104 of the stent to conform to the wall of the left atrium 2. In this example the bottom struts of the cells of the atrial portion 104 of the stent curve downward to connect to the neck region 109, which transitions at an angle range of 65°-120° to the ventricular portion 110 of the stent.

In an optional aspect, the stent tips 117 on the atrial portion 104 of the stent can be configured with a curvature such that they lie substantially parallel to the mitral annulus in operation.

In one exemplary aspect, the atrial portion 104 of the stent can be configured with two rows of cells. In this aspect, the row of cells near the neck region 109 have smaller dimensions than the other row of cells towards the stent tip 117. In this aspect, the further row of cells can be configured with bend struts with angle between 90°-145°.

In another aspect, the cells in two rows of the atrial portion 104 of the stent can be of the same dimensions.

In one aspect, a neck region 109 joins the atrial 104 and ventricular 110 portions of the stent. In this aspect, the neck region 109 is continuous with the upper atrial 104 and lower ventricular 110 portions of the stent. The neck region 109 can be configured with at least one row of cells, e.g., with a height of approximately one to seven millimeters (1.0-7.0 mm). The top portion of the neck 109 can be curved or angled to ease the transition between the atrial 104 and neck 109 portions of the stent. Likewise, the bottom portion of the neck 109 can be curved or angled to ease the transition between the neck 109 and ventricular 110 portions of the stent.

In one exemplary aspect, referring to FIG. 3A, the neck region 109 includes a single row of cells. The cells in the neck regions 109 are formed by the struts on the atrial portion 104 and struts on the ventricular portion 110: the lower struts of the atrial portion 104, form a collapsible half-cell, connect to an elongated, thickened straight strut, and the top struts on the ventricular portion 110 form the other half of the collapsible cell. In this example, the neck region 109 is configured to bend so that the angle between the atrial portion 104 and the ventricular portion 110 ranges from about 650 to 120°. In this aspect, the atrial portion 104 of the stent is nearly parallel to the annulus.

In one aspect, shown in FIG. 3A, the ventricular portion 110 of the stent can assume an asymmetric, semi-conical or semi-circular cross-sectional profile.

In one exemplary aspect, the ventricular portion 110 of the stent is configured to span at least some or all of the posterior leaflet 10 of the native mitral valve 4. Optionally, the lateral edges 112 of the stent can extend circumferentially to the native mitral commissures 14 (not shown, see, e.g., FIG. 1B) to ensure there is at least partial or full coaptation between the native anterior mitral leaflet 6 and at least one prosthetic leaflet 200 coupled to the inner surface of the ventricular portion 110 of the stent.

In one aspect, in the expanded configuration, the stent 100 is configured to have an anterior-posterior (AP) dimension. In exemplary embodiments, the AP dimension at the ventricular level ranges from about ten to forty millimeters (10-40 mm) and/or the AP dimension at the atrial level ranges from about twenty to sixty millimeters (20-60 mm). In further examples, the anterior commissure to posterior commissure length, namely the commissure-to-commissure (CC) length can range from about twenty to sixty millimeters (20-60 mm) and/or the CC length can range from about thirty to ninety millimeters (30-90 mm) at the atrial level. The ventricular portion 110 of the stent is configured to form a "C-shape" in the operative position, thereby displacing the native posterior mitral leaflets 10 and allowing for at least one prosthetic leaflet 200 to extend radially up to the lateral edges of the stent 100 to coapt with the native anterior leaflet 6.

In one aspect, the ventricular portion 110 of the stent is configured with different heights along its circumference such that it does not interfere with the papillary muscles 14.

In a currently preferred embodiment of the ventricular portion 110 of the stent, the stent height in the center of the valve can range between about ten and forty millimeters) 10-40 mm) and the stent height at the lateral sides of the stent 112 can range between about five and fifteen millimeters (5-15 mm).

In one aspect, the ventricular portion 110 of the stent can comprise at least one row of cells. A row of cells can span all or a portion of the circumference of the ventricular portion 110 of the stent.

In one exemplary aspect, the ventricular portion 110 of the stent is configured to have three rows of cells. Rows I, II, and III 134,135,136 are configured to be at the top, middle, and bottom of the ventricular portion 110 of the stent, respectively. Each row is configured to have a plurality of conjoined struts that assume a collapsible diamond-shaped cell with a height of 7-8 mm and a width of 4-6 mm. Each row can include the same number of cells, or differ in their number of cells.

In one aspect, Row I cells 134 are attached to the neck region 109 at the top of the cell, and share Row II cells 135 at the lower struts 101. Optionally, one or more of the Row I cells 134 can be configured to be covered with the sealing skirt 300 to facilitate prosthetic leaflet 200 coupling and prevent leakage.

In an additional aspect, Row II cells 155 share Row I cells 154 to the top and Row III cells 156 to the bottom. In one regard, a plurality of Row II cells 155 positioned behind the at least one prosthetic leaflet 200 can optionally be configured to be open cells, without being covered by the skirt 300. This configuration promotes radial extension of the at least one prosthetic leaflet 200 and prevents blood stagnation behind the leaflet(s) 200. The cells which are covered by the skirt 300 include a leaflet attachment line, e.g., to couple a plurality of prosthetic leaflets 200 to the stent 100.

In another aspect, Row III cells 136 are shared with Row II cells 135 to the top and are free standing on the bottom. The two lateral edges 112 are configured to be covered with at least one layer of fabric 300. Portions of the Row III cells 136 corresponding to prosthetic leaflet 200 attachment regions can be configured to be covered with the sealing skirt 300, while other regions can optionally be left open without a skirt 300.

In one aspect, the height and width of the cells in each row can be the same. In another aspect, the height and width of the cells in each row can be different.

In one aspect, the ventricular portion 110 of the stent can be configured with a hemi-conical shape where the diameter is smallest near the neck portion 109 and increases moving downward towards the ventricle 3 in operation.

Figure 4:
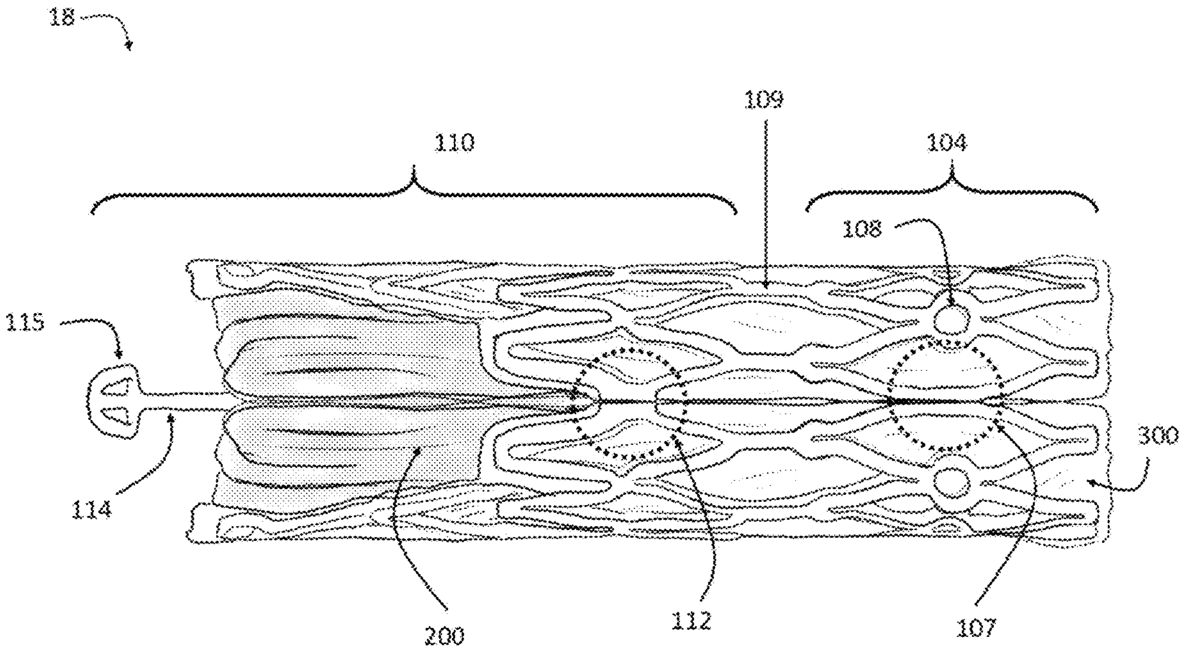
FIG. 4 is a schematic view of an exemplary embodiment of a prosthetic hemi-valve in the crimped configuration. The lateral free edges of the stent are configured with binding sites to engage each other during the crimping process to keep the valve in a cylindrical configuration throughout crimping. The elongated member is the longest part of the crimped device, such that a portion of the delivery system can be configured to engage the tab on the tip of the elongated member without affecting the rest of the valve.

In one optional aspect, referring to FIG. 4, the stent can include binding sites on the lateral edges 112 on the ventricular portion 110 of the stent to facilitate crimping. In this aspect, the binding sites 112 can be configured to include at least one row of the ventricular cells and optionally, at least one row of the atrial cells. In this aspect, the lateral edges 112 of the stent can be configured with corresponding shapes such that they fit together snugly and keep the stent in a cylindrical configuration throughout crimping. In one exemplary aspect, the binding site 112 can be configured as straight, zigzag, semi-circular, semi-oval, or rectangular shaped struts.

In one aspect, the binding junction 103 can be configured as a non-straight section on the lateral edges 112 wherein opposing lateral edges 112 are configured to engage each other during stent crimping 18.

In one aspect, one or more cell struts can be configured with through-holes 113 that provide a mechanism for attachment of at least a portion of the prosthetic leaflet 200 to the frame without the need for skirt 300 material on that cell.

In an exemplary embodiment of the prosthetic hemi-valve device 1, one or more struts in Row III 136 of the ventricular portion 110 of the stent can be configured with through-holes 113 for attachment of at least one prosthetic leaflet legs 205 directly to the strut. In this aspect, the plurality of through-holes 113 can range from about 0.1 mm-1 mm in diameter. Optionally, the struts containing the through-holes 113 can be configured to be approximately 1.1 to 2.5 times wider than other struts to accommodate for the presence of the through-holes 113.

In an exemplary embodiment, the ventricular portion 110 of the stent can be configured such that the at least one prosthetic leaflet commissures 201 attach to the frame 100 at one or more of the ventricular stent tips 118, such that the stent tips 118 can radially deflect when the leaflet 200 is loaded.

Referring to FIG. 3A, in one exemplary aspect, the ventricular portion 110 of the stent can be configured with a sting-ray shape, which extends furthest in the ventricle 3 in the center, and is shorter on the lateral sides 112 to prevent interference with the native papillary muscles 16 in operation.

Figure 3B:
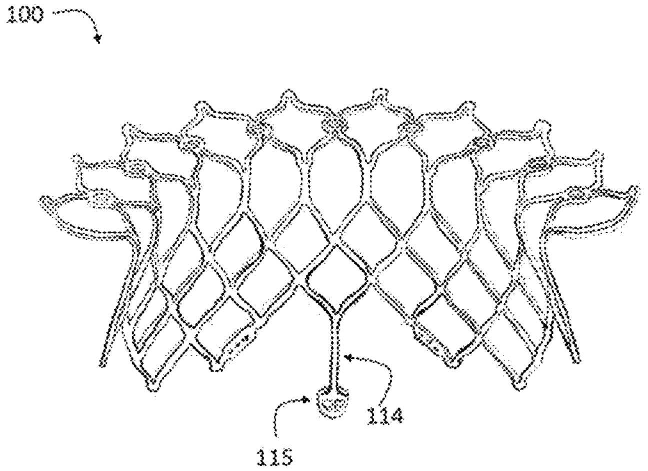
FIG. 3B shows an alternative embodiment of the stent frame, wherein a central extended member with a tab extends from the tip of the center cell of the ventricular portion of the stent.
Figure 3C:
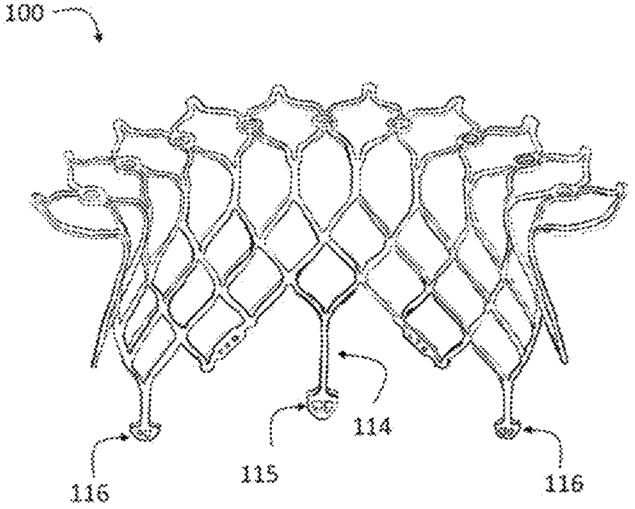
FIG. 3C shows an alternative embodiment of the stent frame, wherein a central and at least one peripheral extended member with a tab extends downward from the ventricular portion of the stent.

Referring to FIGS. 3B-3C, in the string-ray design of the stent 100, at least one string-ray tail or extended member 114 can be configured to extend vertically downwards from the bottom strut junction 103 of the ventricular section 110 of the stent. One or more extended members 114 can be extended from the cell at the center of the bottom portion of the ventricular section 110 of the stent, or optionally, from any other parts of the stent 100. In exemplary embodiments, the extended member 114 can have a width of about 0.3-5.5 mm and a length of about 1.0 to 10.0 mm. The distal end of the extended member 114 can be configured with a central tab 115.

In another aspect, the extended member 114 with the central tab 116 can extend from different cells along the circumference of the ventricular portion 110 of the stent. In this aspect, the length of the extended member 114 can be about 1.0 to 5.0 mm so that it will not interfere with the native surrounding structures.

In another aspect, referring to FIGS. 3B-3C, at least one peripheral tab 116 can be configured to attach to different cells along the circumference of the ventricular portion 110 of the stent, without the extended member 114.

In another aspect, at least a portion of the ventricular portion 110 is configured such that the lowest tips 118 bend inwards radially. In an example, the bend angle can be configured to be between 10°-50° with respect to the axial direction of the stent 100.

In one exemplary aspect, the tabs 115, 116 can comprise at least one hole. The tabs 115,116 can be configured with various shapes for various delivery system engagement mechanisms, including but not limited to magnetic engagement mechanisms, male-female coupling engagement mechanisms, turning locks, etc., which can selectively engage at least a portion of the delivery system throughout the valve deployment process, thereby stabilizing the deployment process.

In one aspect, the tabs 115, 116 can be made of the same as or different materials to the stent 100, and can be permanently connected to the stent 110 via a variety of attachment means such as adhesives, magnetic engagement, etc. The tabs 115,116 and their extension structures 114 can be connected to the delivery system in different directions. In a further aspect, the tabs 115,116 can be detached from the stent 100 after the stent deployment.

In one aspect, at least one prosthetic leaflet 200 is mounted to a skirt 300 that is coupled to the ventricular portion of the stent 110 via non-absorbable sutures. The stent 100 can be configured to permit the natural dynamic motion of any remaining native leaflet(s) to coapt with the prosthetic leaflet(s) 200.

In one aspect, the ventricular portion 110 of the stent is configured to displace the native posterior mitral leaflet 10 in the left ventricular chamber 3 of the heart and position at least one prosthetic leaflet 200 in its place.

A sealing skirt 300 is coupled to at least a portion of the inner and outer surfaces of the stent 100 to prevent leakage between the prosthetic hemi valve frame 100 and at least one prosthetic leaflet 200, and to also provide a base for attachment of the at least one prosthetic leaflet 200.

The skirt 300 can be made of a synthetic or natural biocompatible non-permeable material including, but not limited to, polymers, fabric, biological materials, and the like. The skirt 300 may be cut from a similar or different material as the leaflets 200 to ensure compatibility within the body. The skirt 300 can be laser cut, die cut, or manually cut to optimize uniformity and accuracy of the desired dimensions. In an exemplary embodiment, the skirt 300 thickness can range between about 0.1 mm and 0.15 mm.

In one aspect, the skirt 300 can be configured to exhibit a biaxial orientation, with the fibers aligned circumferentially, thus allowing the skirt 300 to stretch axially during the crimping and release process such that the skirt 300 can conform to the elongated stent shape without tearing or damaging the prosthetic leaflets 200.

Optionally, the non-permeable sealing skirt 300 further comprises atrial 302 and ventricular 301 portions. In this option, the atrial 302 and ventricular 301 portions can be configured as one piece. In another option, the atrial 302 and ventricular 301 portions can be configured as two separate pieces.

In one aspect, the skirt 300 is coupled to the stent 100 via one or more of sutures, adhesive, and/or other biocompatible materials.

In one aspect, a ventricular skirt 301 is used as a structure to attach the prosthetic leaflets 200 to the stent 100. In this aspect, the ventricular skirt 301 can be configured to cover at least a portion of the ventricular portion 110 of the stent to facilitate attachment of the prosthetic leaflet 200.

In one aspect, the ventricular portion of the skirt 301 is configured with a plurality of tabs configured to wrap around stent struts at the commissural regions to prevent skirt translation during crimping.

In one aspect, the ventricular skirt 301 can be configured to conform to the inner surface of the ventricular portion 110 of the stent. The upper edge of the ventricular skirt covers the neck region 109 of the stent and also provides a path for a connection line 303 to attach the ventricular skirt 301 to the atrial skirt 302. The ventricular skirt 301 is configured to cover select cells on the ventricular portion 110 of the stent.

In one aspect, prosthetic leaflets 200 are configured to attach to the ventricular skirt 301 along an engineering-designed parabolic leaflet attachment line. The ventricular skirt 301 is configured to cover the stent portions 110 where the leaflet attachment line should align to facilitate attachment of the at least one prosthetic leaflet 200 to the stent 100.

Figure 5:
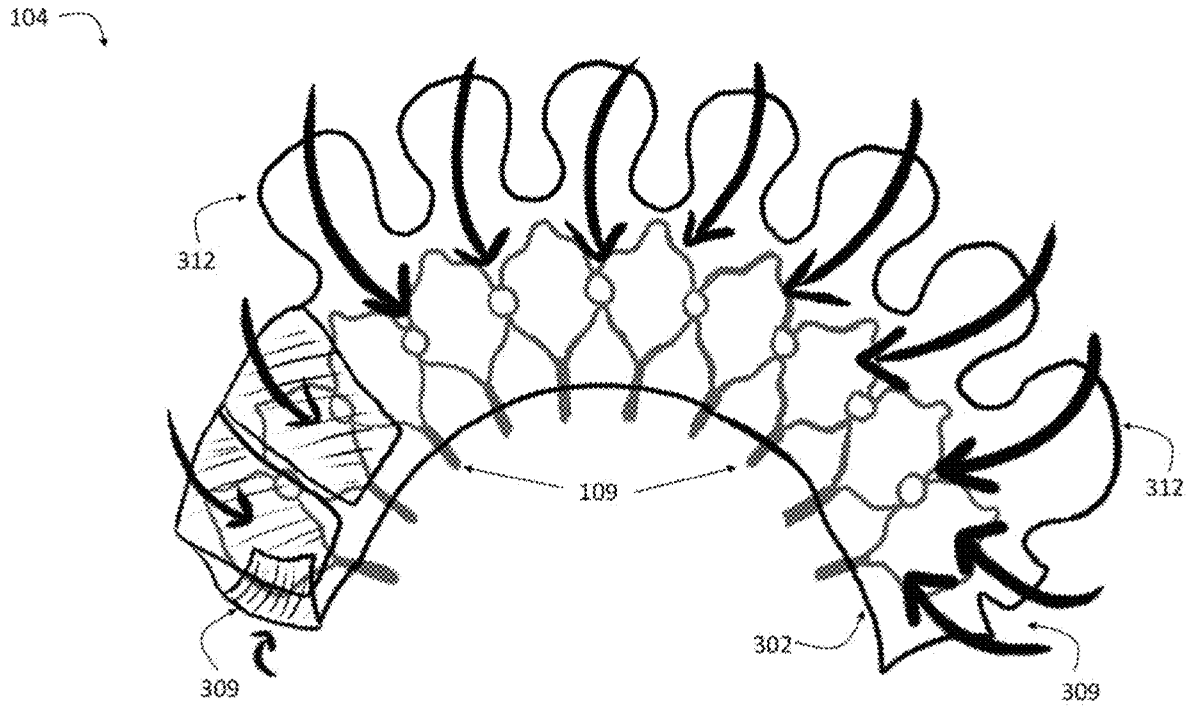
FIG. 5 is a schematic view of an atrial skirt creating a paravalvular seal around the atrial portion of a valve, such as that the prosthetic hemi-valve of FIG. 2B.

In one embodiment, as seen in FIG. 5, a plurality of enlarged tabs 312 of the atrial skirt 302 are folded to create a plurality of pockets for paravalvular sealing. In a further embodiment, folding over the enlarged tabs 312 creates a uniform layer of skirt 302 on the back side of the valve 100 that comes into direct contact with the atrial tissue 2. This layer of folded over enlarged tabs 312 prevents paravalvular leakage.

In one aspect, an atrial skirt 302 is used to encourage paravalvular sealing in the atrium 2, and further anchoring the valve 1 to the annulus. The atrial skirt 302 is configured to conform to the unique curvature of the atrial portion 104 of the stent.

In one aspect, the atrial skirt 302 can be configured with a material that can be penetrated by the DGF member head such that after the valve 1 is deployed and locked into place, additional DGF members can be implanted through the atrial skirt 302 to further fasten the valve 1.

In the example shown in FIG. 5, there are two side tabs 309 on the atrial skirt 302. These tabs 309 are configured to fold over the lateral edges 106 of the atrial portion of the stent to create a side skirt. The lower portion of the side tab 306 on the atrial skirt 302 engages with a large tab on the ventricular skirt 301 by folding under the corresponding large tab. The large tab on the ventricular skirt 301 and side tab 309 on the atrial skirt 302 fold over themselves. This feature is notable, as this region comes into direct contact with the commissures 14 of the native mitral valve 4. The side skirt thereby provides a dual function. First, the side skirt prevents the sharp edges of the stent 100 from cutting into the native mitral commissure 14. Second, the side skirt provides an attachment for a sealing ring 316 to create a paravalvular seal around the edges of the valve 1.

Figure 6:
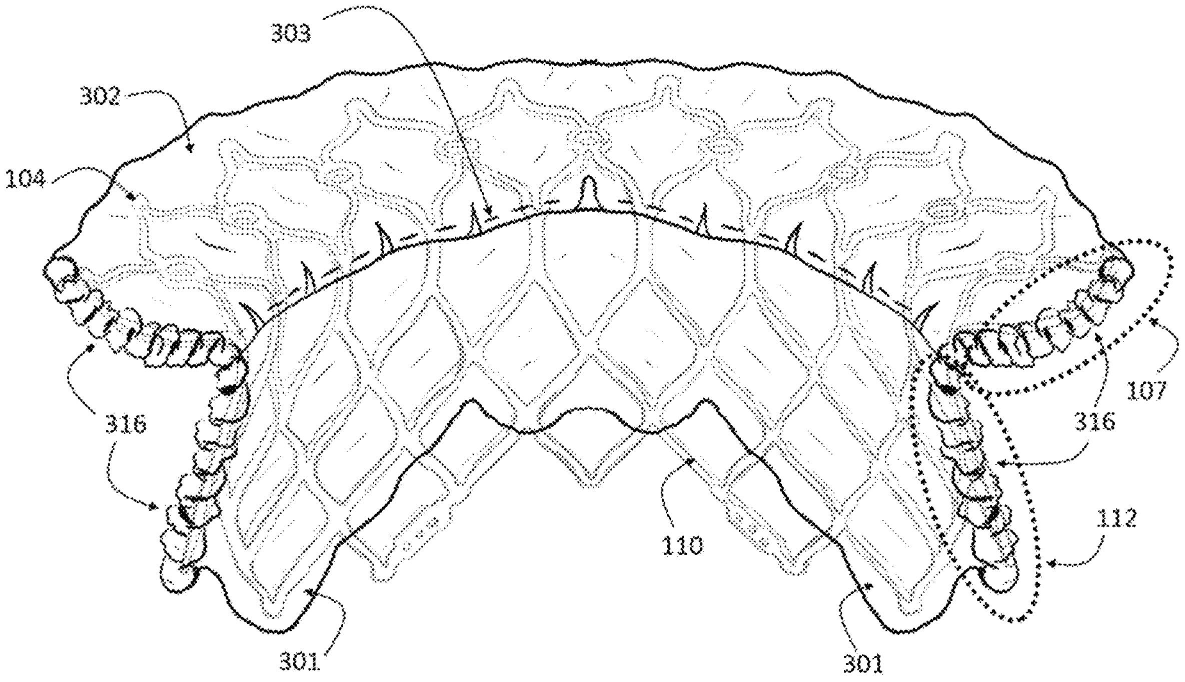
FIG. 6 is a schematic view of a frame covered with atrial and ventricular sealing skirts and a sealing ring on both lateral edges.

Optionally, as seen in FIG. 6, a sealing ring 316 can be affixed to the lateral edges 107,112 of the valve to create a paravalvular seal along the commissures 14 of the native mitral valve 4 and also provide cushioning between the lateral edges 107, 112 of the stent 100 and the surrounding tissues.

In one embodiment, a sealing ring 316 can be affixed to at least a portion of the atrial portion 104 of the frame to create a paravalvular seal along the annulus.

The sealing ring 316 can be made of a flexible synthetic or natural biocompatible material including, but not limited to, polymers, fabric, biological material, and the like. The sealing ring 316 can surround the lateral and top edges of the valve 1 that can come into contact with the native tissue, avoiding the bottom edge of the valve 1 as to not interfere with leaflet motion in operation. The sealing ring 316 may be permanently fixed to the valve 1, e.g., with one or more sutures, adhesives, and/or other biocompatible materials.

In one aspect of the prosthetic hemi-valve device 1, at least one dome-shaped prosthetic leaflet 200 can be mounted on the inner surface of the frame. In one aspect, at least one prosthetic leaflet 200 can be mounted to the inner surface of the lower ventricular portion 110 of the frame. It is contemplated that at least one prosthetic leaflet 200 can comprise a plurality of leaflets wherein all of the prosthetic leaflets 200 can have the same shape and size or wherein one or more of the plurality of leaflets 200 have different shapes and/or sizes.

Figure 7:
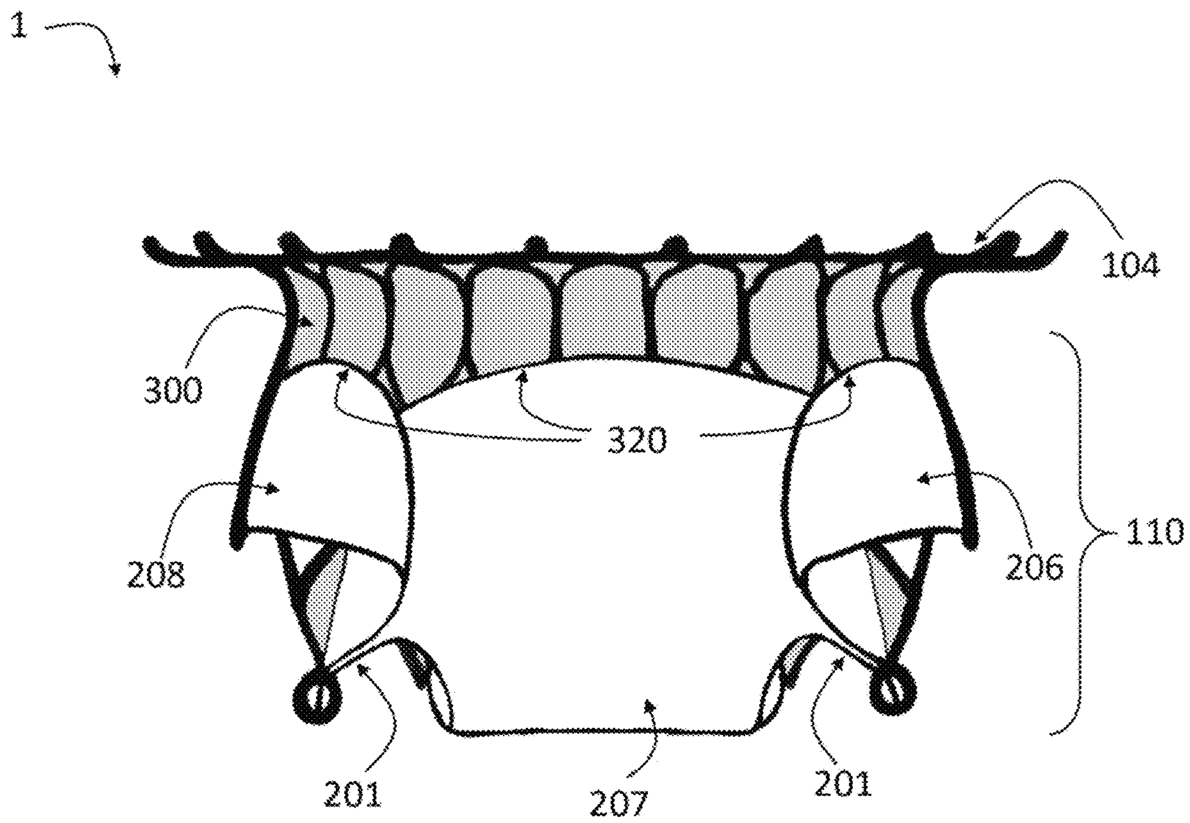
FIG. 7 is a schematic view of one embodiment of a prosthetic hemi-valve with three dome-shaped prosthetic leaflets mounted on the inner surface of a frame. In this aspect, the assembly of prosthetic leaflets include one larger central leaflet and two smaller lateral leaflets.
Figure 8:
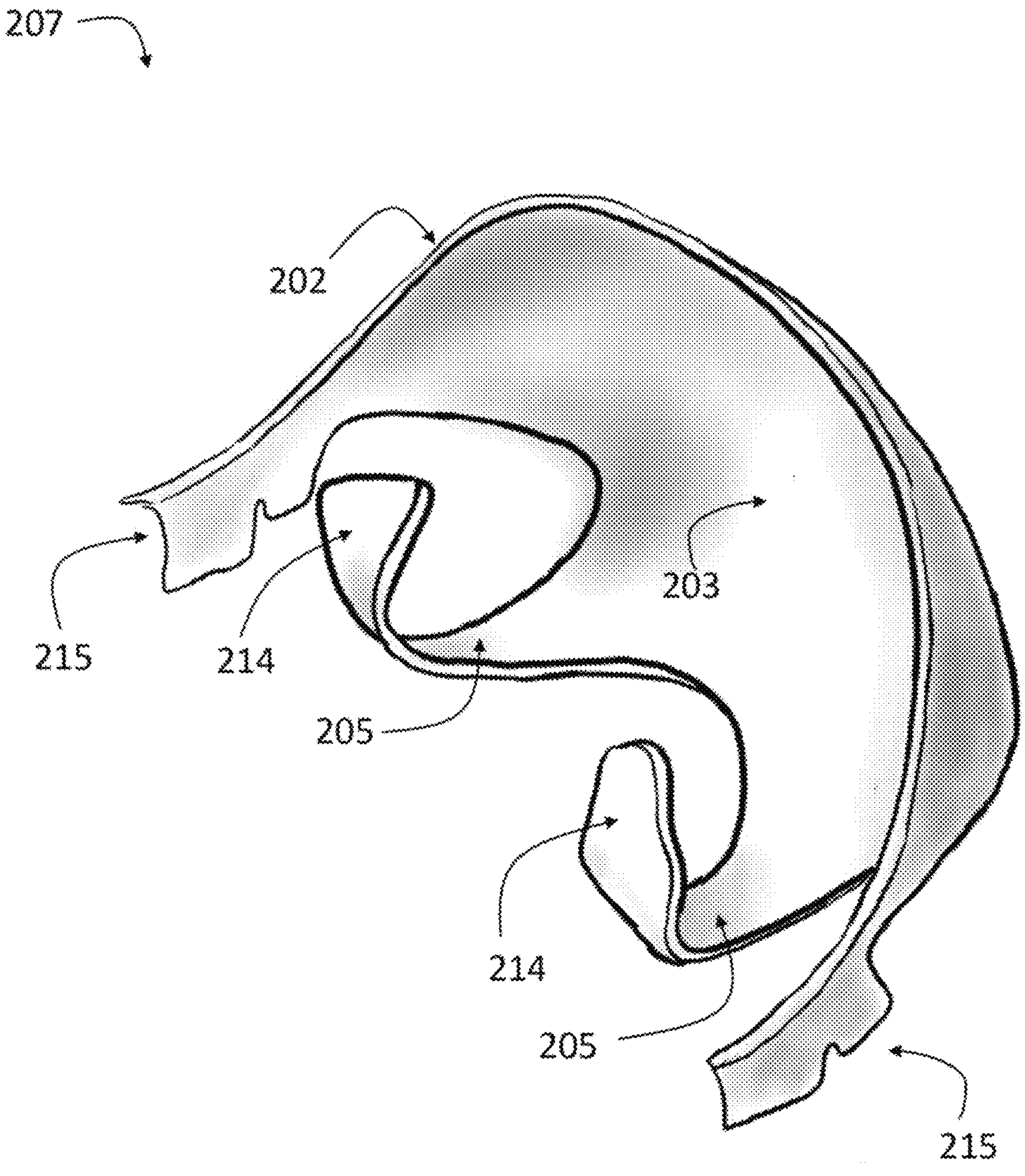
FIG. 8 shows an exemplary embodiment of a large central prosthetic leaflet which comprises a dome-shaped body, two legs, and two arms.

In an exemplary embodiment shown in FIGS. 7 and 8, each dome-shaped prosthetic leaflet 207 can comprise two commissures 201, a curved attachment edge 202, a belly region 203, a coaptation region 204 and, optionally, at least one arm 215, and at least one leg 205. In one exemplary aspect, the attachment edge 202 of the at least one leaflet 207 can be mounted to an inner lumen of the stent 100 or skirt 300, e.g., using non-absorbable sutures. In another aspect, the foot 214, i.e., the free end of the at least one leg 205, can be mounted to an inner lumen of the stent 100 or skirt 300, e.g., using non-absorbable sutures.

In one aspect, the dome-shaped prosthetic leaflet(s) 207 can be configured to be mobile throughout the cardiac cycle such that the belly and coaptation regions extend radially inward from the frame 100 at systole to prevent transvalvular central or commissural leakage, and to move towards the frame 100 during diastole to allow ventricular filling. The prosthetic leaflet commissures 201, attachment edge 202, and feet 214 of the legs 205 that are attached to the stent 100 are immobile with respect to the stent 100.

In one aspect, the at least one prosthetic leaflet 207 can be configured with at least one arm 215 extending from the leaflet commissure 201.

In one aspect, the dome-shaped leaflet(s) 207 can be configured such that they exhibit limited collapsibility and radial extension such that they do not hit the frame 100 during valve opening, and cannot extend beyond the frame 100 radius during valve closing, in operation.

In one aspect, the dome-shaped prosthetic leaflet(s) 207 can be configured to coapt with the native anterior mitral leaflet 6 during systole in operation. Referring to FIG. 1A of the healthy native mitral valve 4 during systole, the posterior mitral leaflet 10 extends radially to form a C-shape to coapt with the anterior mitral leaflet 6. In a patient with functional mitral regurgitation, the native leaflets 6,10 would not be able to extend far enough towards each other in order to coapt fully. It is contemplated, as seen in FIG. 2B, that the prosthetic leaflet 200 can be configured to form the C-shape of the native posterior leaflet 10 and extend beyond this line, to a D-shape, to coapt with the native anterior mitral leaflet 6 in patients with functional mitral regurgitation.

The prosthetic hemi-valve device 1 anchoring mechanism can be configured to resist separation from the posterior mitral annulus during systole and device migration in operation. In one aspect, the prosthetic hemi-valve device 1 can be configured to cover about half or ⅔ of the mitral orifice during systole. In this aspect, given the half valve nature of the prosthetic hemi-valve 1, only about half of the total force induced by the blood flow during systole will act on the prosthetic hemi-valve device 1, thus only half of the total force will act on the anchoring mechanism. The rest of the force induced by the blood flow will act on the native anterior mitral leaflet 6 and annulus. As such, it is contemplated that a prosthetic hemi-valve 1 may be easier to secure to the mitral annulus compared to a full circumference prosthetic valve. One skilled in the art can appreciate that anchoring of full circumference prosthetic valve devices in the mitral position continues to be a challenge.

In one aspect of the prosthetic hemi-valve device 1, with continued reference to FIG. 2B, the plurality of dome-shaped prosthetic leaflets 200 can be formed from a flat piece of flexible material which is sewn or otherwise attached to the frame 100 such that they can be mobile throughout the cardiac cycle and resist separation from the frame 100. In another aspect, the plurality of dome-shaped prosthetic leaflets 200 can be pre-shaped into a 3D dome geometry by casting, deforming, molding, braiding, heat or chemical treatment, 3D printing, electro-spinning, or other fabrication methods.

In one aspect, the plurality of prosthetic leaflets 200 can comprise pericardial tissue, or other biological or tissue engineered materials, polymeric, fabric, or flexible metallic material, and the like. In this aspect, it is contemplated that a moveable, flexible prosthetic leaflet 200 would exhibit give when interacting with a native anterior leaflet 6, and thus would induce minimal damage to a native valve leaflet 6 due to repeated contact.

It is contemplated that due to the hemi-valve 1 nature of the device, the prosthetic leaflet 200 can be configured with a thicker leaflet material than other prosthetic mitral valves intended to be implanted via catheter, and still have a small crimped device profile which is desirable for procedure feasibility and patient safety. One skilled in the art can appreciate that a thicker prosthetic leaflet 200 is desirable for prosthetic valve 1 durability.

Figure 1B:
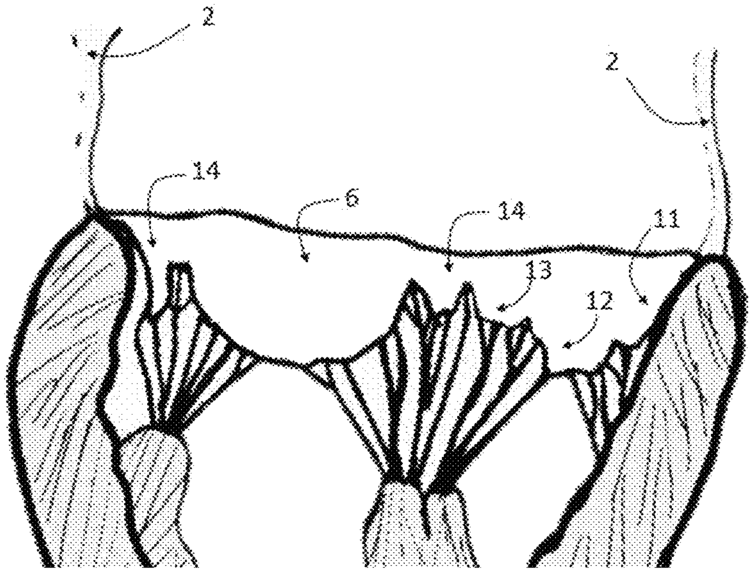
FIG. 1B is a prospective view of the native mitral valve after the left ventricle has been splayed open to reveal the anatomy of the mitral leaflets: the mitral valve leaflets are divided into two portions: the anterior and posterior portions, and each portion is subdivided into three sections. The posterior leaflet comprises three adjoined semi-lunar shapes, namely the P1, P2, and P3 cusps. The P2 cusp is the largest and extends the furthest into the ventricle, while the P1 and P3 cusps are smaller and shorter. The anterior mitral leaflet similarly has regions which coapt with P1, P2, and P3, respectively, in systole.

Referring to FIG. 1B, the native posterior mitral leaflet 10 comprises three adjoined semilunar shapes, namely the P1, P2, and P3 cusps 11,12,13. The P2 12 cusp is the largest and extends the furthest into the ventricle 3, while the P1 and P3 cusps 11,13 are smaller and shorter, particularly on the lateral sides. In one exemplary embodiment of the prosthetic hemi-valve device 1, referring to FIG. 7, the plurality of prosthetic leaflets 200 can comprise two smaller lateral leaflets 206, 208, and larger central leaflet 207 mimicking the native posterior leaflet 10 anatomy.

Referring to FIG. 7 again, in one aspect, the prosthetic leaflets 200 can be configured as a plurality of dome-shaped structures extending inward radially away from the stent 100. In another optional aspect, the prosthetic P2 (PP2) leaflet 207 can extend further down into the left ventricle 3 in operation than the lateral sides of the prosthetic P1 (PP1) and prosthetic P3 (PP3) leaflets 206, 208, similar to the native posterior mitral leaflet 10.

Figure 9A:
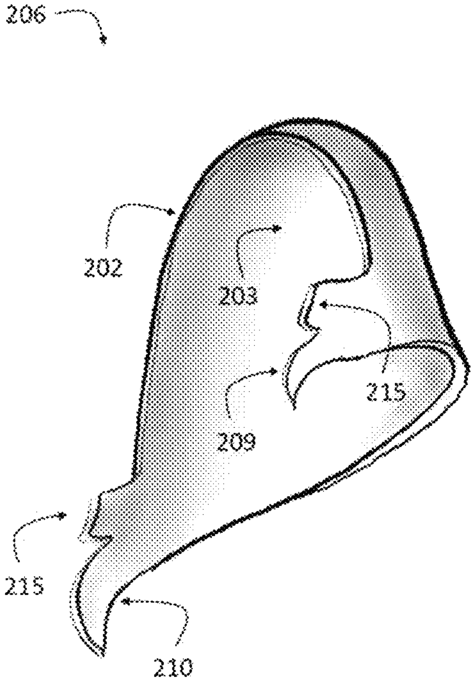
FIGS. 9A and 9B show examples of smaller lateral prosthetic leaflets, each including a dome-shaped body and two arms.
Figure 9B:
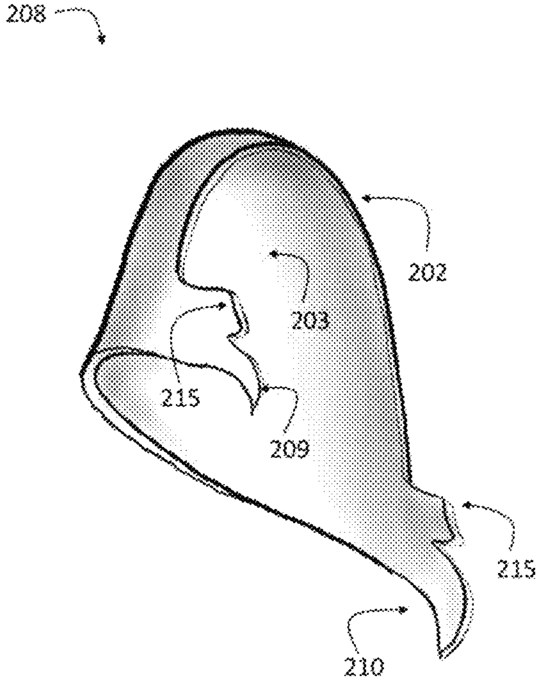

In the exemplary embodiments shown in FIGS. 9A and 9B, the PP1 and PP3 leaflets 206, 208 can be configured as mirror images of each other, with a shorter height on the lateral edges corresponding to a shorter frame height at the lateral edges, and a taller height on the medial edges to align the medial PP1 and PP3 commissures 210 with the PP2 commissures. It can also be appreciated by one skilled in the art, that having shorter PP1 and PP3 lateral commissures 209, the crimped profile of the prosthetic hemi-valve device 1 can be desirably reduced, because the amount of leaflet material is greatest at the leaflet commissures 201, and by having the lateral commissures 209 at a different height than the medial commissures 210, the amount of material at the medial commissures 210 is reduced and thus can be crimped to a smaller diameter.

In one embodiment of the prosthetic hemi-valve device 1, the prosthetic leaflets 200 can be configured to attach to the frame 100 starting just below the neck region 109 of the frame 100 and extending axially to the tips of the ventricular portion 118 of the frame and cover the circumference of the ventricular portion 110 of the frame. In other optional aspects, the prosthetic leaflets 200 can be configured to wrap around the lateral edges of the frame 112 or only cover a portion of the frame 100 circumference. Further, the prosthetic leaflets 200 can be configured to extend axially from the upper flared 104 or neck portions 109 of the frame to the ventricular portion 110 of the frame. Optionally, the prosthetic leaflet 200 can be configured to cover only a portion of the ventricular portion 110 of the frame.

In one aspect, the prosthetic leaflets 200 are attached to the frame 100 along a leaflet attachment line 320 that comprises a plurality of parabolic shapes where each parabolic shape delineates a prosthetic leaflet 200.

In one aspect, the leaflet attachment line 320 can be configured to be symmetric about the center of the skirt 300. In an optional aspect, the leaflet attachment line 320 can be configured to be asymmetric.

In an exemplary embodiment, as shown in FIG. 7, the leaflet attachment line 320 is configured as three parabolic shapes next to each other for the attachment of three distinct prosthetic leaflets 200. In this aspect, the leaflet attachment lines for PP1, PP2, and PP3 206, 207, 208 can be configured with the same size and shape or differing size and shape, and can be either symmetric or asymmetric.

Optionally, the PP2 leaflet attachment line 320 is configured to span about one third to two thirds of the stent 100 circumference and be symmetric about its axial midline.

In addition or alternatively, the PP1 and PP3 leaflet attachment lines 320 can be configured as mirror images of each other, and to span about one sixth to one third of the stent circumference. The PP1 and PP3 leaflet attachment lines 320 can be configured to be shorter on the lateral edges such that they are asymmetric about their respective axial midlines.

In one aspect, the plurality of leaflets 200 can be configured as separate individual pieces of flexible material that are affixed to the frame 100 along each of the parabolic leaflet attachment lines 320. Each leaflet 206, 207, 208 can be made of the same or different material. In another optional aspect, the plurality of leaflets 200 can be formed from one single piece of flexible material by affixing the material to the frame 100 along each of the parabolic leaflet attachment lines 320.

In one aspect, the parabolic shape of the leaflet attachment lines 320 can be configured to distribute blood flow induced forces throughout the prosthetic leaflets 200 and frame 100. One skilled in the art can appreciate that by distributing forces throughout the device 1, localized high stress regions which can negatively impact device 1 durability, can be prevented.

In one aspect, the leaflet attachment line 320 can be configured to align with the stent struts, particularly at high stress regions such that blood flow forces acting on the leaflet 200 will be, in part, distributed directly to the stent 100. In a further aspect, the leaflet attachment line 320 can be configured such that the prosthetic leaflet commissures 201 align with the ventricular stent tips 118 such that the ventricular stent tips 118 can deflect radially inwards, e.g., about 5° to 15° when a pressure load is applied to the prosthetic leaflets 200. In this aspect, the stent-tip 118 deflection can cushion the prosthetic leaflets 200 from forces acting on them which has been shown to be important for bioprosthetic valve 1 durability.

In another optional aspect, the leaflet attachment line 320 can be configured such that the prosthetic leaflet commissures 201 align with tabs 116 extending from the lower ventricular portion 110 of the frame, as seen in FIG. 3C. In this aspect, the tab 116 can be configured with at least one through-hole to facilitate attachment of the commissure 201 to the frame 100. Optionally, the tab 116 can be configured on the end of an extended member 115 configured such that the tab can deflect radially inwards, e.g., about 5° to 15° when a pressure load is applied to the prosthetic leaflets 200.

In one aspect, the prosthetic leaflets 200 can be mounted on the frame 100 such that the stent cells behind the belly region 203 of the prosthetic leaflets 200 are open with no skirt 300 material. It is contemplated that by leaving these cells open, blood flow can reach the belly region 203 of the prosthetic leaflet 200 more quickly such that the prosthetic leaflets 200 can extend quickly to cover the mitral valve orifice in systole and prevent regurgitation. Further in this aspect, it is contemplated that by increasing blood washout between the prosthetic leaflets 200 and the frame 100, the incidence of thrombosis formation due to flow stagnation can be reduced.

Referring to FIG. 8, in an exemplary embodiment, the larger PP2 leaflet 207 can be configured with a plurality of leg structures 205, the feet 214 of which attach to the ventricular portion of the frame 110. In this aspect, the leaflet legs 205 are configured to limit radial extension of the leaflet belly 203 and coaptation regions 204 and prevent billowing and prolapse. Further, the leaflet legs 205 can help distribute force throughout the leaflet 200 and frame 100 which is particularly important for larger leaflets experiencing large blood flow induced forces.

It can be appreciated by one skilled in the art that the proper dome shape proportions must be maintained for proper prosthetic leaflet 200 function, i.e., radial extension. For simplicity, consider a two-dimensional dome height-to-width ratio, if the height-to-width ratio is small, the prosthetic leaflet 200 can extend a lot radially, but can also potentially prolapse in operation, and if the height-to-width ratio is large, the prosthetic leaflet 200 radial extension is limited and potentially cannot extend far enough to cover the regurgitant orifice area.

Referring to the example shown in FIG. 8, the PP2 leaflet 207 has a small height-to-width ratio of about 0.4-0.7 which allows a great degree of radial extension however also makes it vulnerable to prolapse. Therefore, the PP2 leaflet 207 is configured with two legs 205 which attach to the frame 100 to limit the PP2 leaflet 207 from extending radially beyond the leg 205 length which is about 70-100% of the anterior-posterior dimension of the frame. In this aspect, the leg structure 205 is a design feature which prevents leaflet prolapse in a leaflet with a small height-to-width ratio and a large degree of radial extension. In this aspect, the length-to-width ratio of the leg structure 205 is about 4 to 7.

Referring to the examples shown in FIGS. 9A and 9B, the PP1 and PP3 leaflets 206, 208 have a large maximum height-to-width ratio of about 1-1.5 which allows a smaller degree of radial extension, thus the PP1 and PP3 leaflet 206, 208 in this embodiment do not require legs 205.

The height-to-width ratio determining leaflet prolapse will also depend on the angle of the ventricular portion 110 of the stent with respect to the atrial portion 104 of the stent, where an angle less than 90° will help prevent prolapse in leaflets with a low height-to-width ratio. Further, the height-to-width ratio will depend on the leaflet 200 opening angle, i.e., the angle made between the two commissures 201 and the center point of the frame 100, where a larger angle will help prevent prolapse in leaflets 200 with a low height-to-width ratio. Therefore, the leaflet 200 height-to-width ratios presented here are meant to be illustrative to demonstrate the effect of the leg structures 205, and are not meant to be limiting.

One skilled in the art can appreciate that as mitral regurgitation progresses in patients, often the mitral annulus becomes increasingly dilated, thus larger degrees of prosthetic leaflet 200 radial extension may be desirable, without necessarily proportional increases in prosthetic leaflet 200 height. Thus, in some aspects, the prosthetic leaflets 200 may require one or more additional leg structures 205, including on the smaller lateral prosthetic leaflets 206,208. In some other aspects, the prosthetic leaflets 200 may require one or more additional leaflets to make it a four- or five-leaflet valve.

One skilled in the art can also appreciate that it is beneficial for the prosthetic hemi-valve device 1 to have prosthetic leaflets 200 with limited radial extension by design, without the need for additional ventricular anchoring and independent of patient characteristics.

In one aspect, the prosthetic leaflet feet 214 at the end of the leaflet legs 205 can be directly attached to the stent 100 at the through-holes 113 for foot attachment 214 such that there is no need for additional skirt material 300 in this region.

Figure 10:
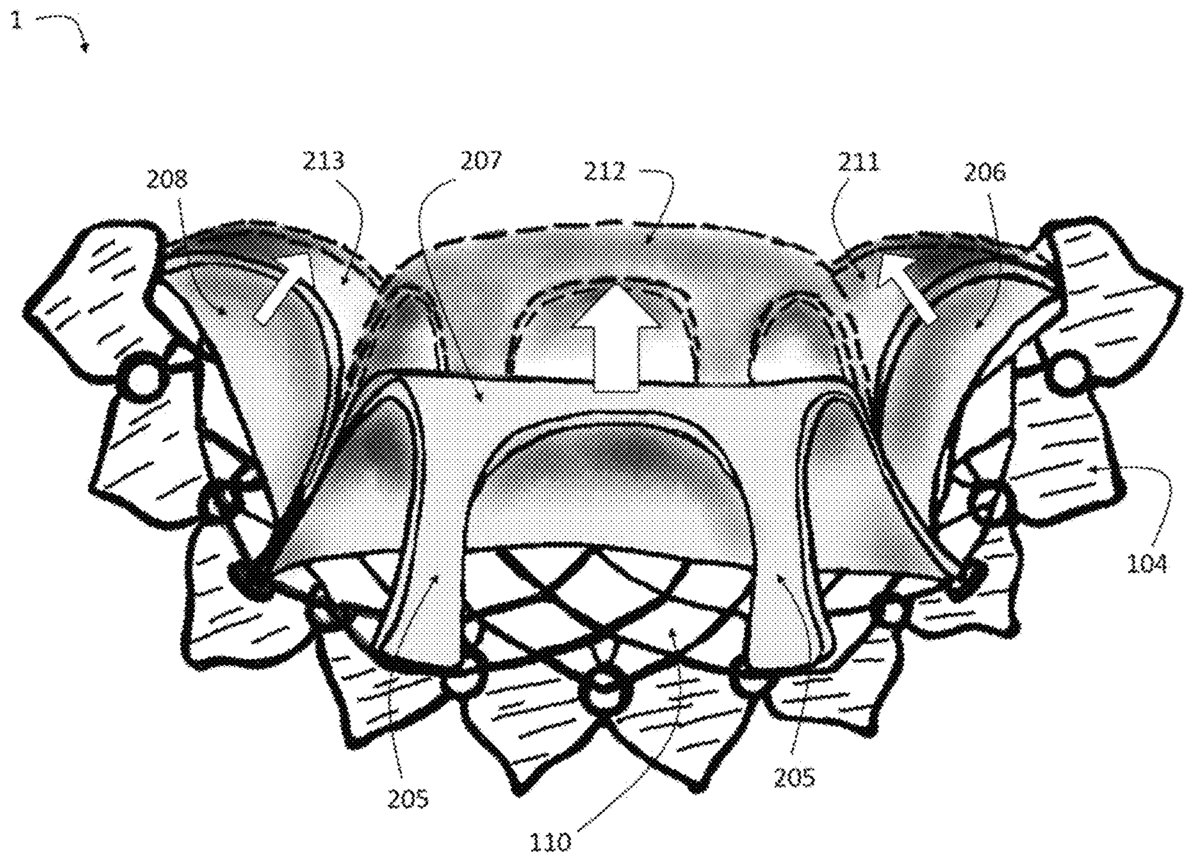
FIG. 10 is a schematic ventricular view of an exemplary aspect of a prosthetic hemi-valve device showing the prosthetic leaflets at a pressurized, systolic state, overlaid with the prosthetic leaflets at an unpressurized, resting state. The prosthetic leaflets extend radially away from the frame under systolic pressure.

Referring to example shown in FIG. 10, the prosthetic leaflets 200 can be configured to form a C-shape at a resting, non-pressurized state similar to that formed by the native posterior mitral leaflet 10 in a healthy mitral valve 4, e.g., as shown in FIG. 2A. Further, the prosthetic leaflets 200 can be configured to form a D-shape at a systolic pressurized state to cover approximately half of the mitral orifice area as shown in FIG. 10.

Referring again to FIG. 10, it can be seen that the addition of the leg structures 205 on the PP2 leaflet 207 helps to create the C-shape such that the PP2 207 extends radially to approximately the same distance across its width, similar to the native P2 leaflet 12. It can be appreciated that without the leg structures 205, the PP2 207 would create a rounded or pointed shape which would extend furthest radially at the center and less on the sides.

FIG. 10 shows a ventricular view of the prosthetic hemi-valve 1 with the prosthetic leaflets 200 at the pressurized condition 211, 212, 213, i.e., systole, overlaid with the prosthetic leaflets at the resting 206,207,208, unpressurized condition. It can be seen that each of the prosthetic leaflets 200 extends radially away from the stent 100 under pressurization, where the degree of extension is greatest in the center of the prosthetic valve 1 at PP2 207, and the smallest at the lateral edges of PP1 and PP3 206,207. FIG. 10 also shows that the legs 205 extending from the bottom of the PP2 207 dome shape to the frame 100 are straight with no twisting at both conditions. It can be seen that at full extension, the prosthetic leaflets 200 together form a D-shape covering nearly the entire lumen of the hemi-valve stent 100. Thus, in operation, the prosthetic leaflets 200 could cover nearly half of the mitral orifice area. One skilled in the art can appreciate that this design can prevent mitral valve leakage in patients that have a native anterior mitral leaflet 6 that covers more than the half of the mitral orifice area during systole.

One skilled in the art can appreciate that typically, the native anterior mitral leaflet 6 covers nearly two thirds of the mitral orifice area during systole. Thus, the prosthetic leaflets 200 in FIG. 2B are not expected to have to extend much if at all beyond their resting state position to coapt with the native anterior mitral leaflet 6. The extra prosthetic leaflet extension enabled by this exemplary design is a precautionary measure to provide a large coaptation zone 204 for the native anterior mitral leaflet 6 with ample coverage of the mitral orifice even in dilated hearts.

Referring to FIG. 10, in an exemplary embodiment, the leg structures 205 can be configured such that when the prosthetic leaflet 200 is loaded, the leg structures 205 extend radially away from the frame 100 in a straight manner, with no twisting of the legs 205.

One skilled in the art can appreciate that the leg structures 205 also act similarly to the native chordae tendineae 15, in that they can prevent over-extension and prolapse of the prosthetic leaflet 200.

In one aspect, the PP1 and PP3 leaflets 206, 208 can also be configured with leg structures 205, particularly for large size prostheses where the PP1 and PP3 leaflets 206,208 are large.

Alternatively, the PP1 and PP3 leaflets 206, 208 can be configured without leg structures 205, particularly for small size prostheses where the PP1 and PP3 leaflets 206,208 are small.

In one aspect, the foot 214 of the leg structure 205 can be configured at an angle to facilitate attachment to an angled strut of the stent with the through-holes 113.

In one aspect, the plurality of leg structures 205 can be configured with a dog-bone shape that is wider at the foot 214 where it attaches to the frame 113, and the base where it extends from the bottom of the dome-shape and relatively narrower in an intermediate region. In this aspect, the added width reduces stress in the leg structure 205 at the regions experiencing the highest forces. One skilled in the art, can appreciate that the dog-bone shape design distributes mechanical stress throughout the leg 205 which is important for durability.

In a further aspect, it is desirable for the plurality of leg structures 205 to be made of a single piece of the same material as the rest of the prosthetic leaflet 200.

In an exemplary embodiment, the PP2 leaflet 207 can be configured with a tallest height in the center (belly 203 and coaptation regions 204) of the leaflet and a shorter height at each of the commissures 201, corresponding to the native posterior mitral leaflet 12 structure, e.g., as shown in FIG. 2B.

In an example of the prosthetic hemi-valve 1, the plurality of dome-shaped prosthetic leaflets 200 are configured as individual flat pieces of flexible material.

In an exemplary aspect, the prosthetic hemi-valve includes a stent 100 which is coupled to a skirt 300 on the inner surface of a stent 100 and a portion of the outer surface of the stent 100. Furthermore, a plurality of prosthetic leaflets 200 are coupled to the inner surface of the skirt 300. In a further aspect, one or more sutures are used to couple the skirt 300 to the stent 100, and the prosthetic leaflets 200 to the skirt 300.

One skilled in the art can appreciate the benefits of a hemi-valve versus a fully-circumferential valve in terms of crimp profile. The reduced stent 100, leaflet 200, and skirt 300 material allows the prosthetic hemi-valve to be crimped into lower profile catheters, enabling a greater at-risk patient population to undergo a heart valve replacement operation.

In one aspect, the prosthetic hemi-valve device 1 is fixed to the posterior mitral annulus by a plurality of DGF members which can be operatively positioned and implanted at desired locations in the native annulus prior to the delivery of the prosthesis 1, e.g., similar to the systems and methods described in the applications incorporated by reference elsewhere herein. In this aspect, the DGF members can guide the subsequent precise positioning and fixation of the prosthesis 1. In a further aspect, the plurality of DGF members can help prevent leakage of blood between the operatively positioned prosthesis 1 and the native mitral annulus.

In one aspect, each DGF member can be configured with removable and permanent components, where removable components can aid in guiding the prosthetic hemi-valve device 1 to the operable position, and then be removed from the patient's body after fixing the prosthesis 1, and permanent components remain in the patient's body to keep the prosthetic hemi-valve device 1 secured to the native annulus.

In an exemplary aspect, each DGF member can comprise head, body, and tail components. In one aspect, each DGF head member can be configured with a coil shape such that it can be operatively inserted and embedded in the annular tissue. In one aspect, each DGF body member can be configured with a DGF locking member 131 to fix the prosthetic hemi-valve device 1 to the native mitral annulus, such as that shown in FIG. 11. In one aspect, the DGF tail member can be configured as a flexible component that extends from the proximal portion of the DGF body, and links the DGF member to the crimped prosthetic hemi-valve 1 within the prosthetic hemi-valve delivery and implantation system. In this aspect, the tail portion can be manipulated on the proximal end of the delivery system to guide and securely maneuver the prosthetic hemi-valve 1 to the native mitral annulus. Optionally, the DGF tail can be configured to be selectively removable, such that it can be removed from the body at the completion of the heart valve leaflet replacement system implantation procedure.

In one aspect, the prosthetic hemi-valve can be configured to engage the DGF locking members 131 via a plurality of holes 108 in the atrial flared portion 104 of the stent. In this aspect, each DGF tail member can be a tether that is configured so that one end of the tether is attached to the DGF body member and the other end of the tether can exit the body. Subsequently, the tether can be inserted through the hole 108 on the atrial flared portion 104 of the stent, such that the prosthetic hemi-valve device 1 can be delivered over the DGF tail members and the atrial flared portion 104 of the stent can be precisely delivered to the DGF body members embedded in the annulus.

In one aspect, the DGF locking member 131 can be configured to pass through the hole 108 on the atrial flared portion 104 of the stent in one direction only.

In one aspect, the DGF locking member 131 can be configured such that it can selectively be compressed to a diameter smaller than the diameter of the hole 108 on the atrial flared portion 104 of the stent, such that it can pass through the hole 108, and subsequently be selectively re-expanded to its original size, larger than the diameter of the hole 108 on the flared portion 104 of the stent to prevent backward motion of the DGF locking member 131 through the hole 108.

Figure 11:
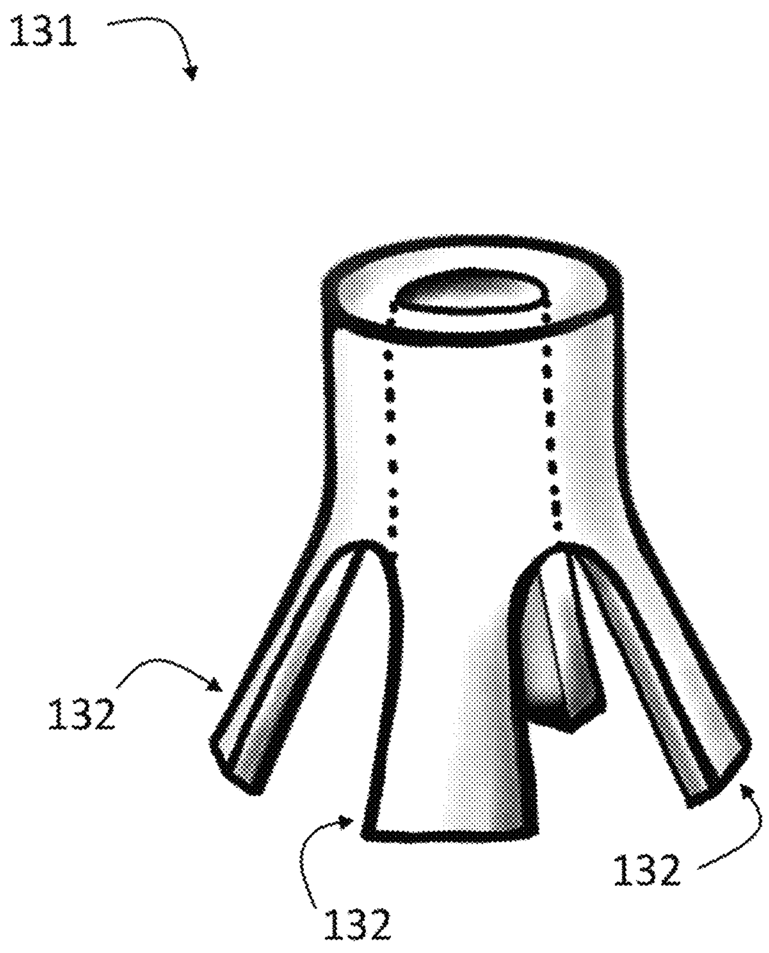
FIG. 11 is a schematic view of an exemplary embodiment of a DGF member locking unit. In this aspect, the locking unit comprises a through-hole for attachment to a tether and a plurality of legs.

In one exemplary aspect, as shown in FIG. 11, each DGF locking member 131 can be configured with a plurality of radially compressible legs 132 forming a cone shape where the proximal tip of the cone shape has a smaller diameter than the hole 108 on the atrial portion 104 of the stent, and the distal base of the cone shape has a larger diameter than the hole 108 on the atrial portion 104 of the stent. In operation, the DGF tails can be tensioned to pull the proximal tips of the DGF locking members 131 into the holes 108 on the atrial portion 104 of the stent, and as the locking member legs 132 come into contact with the edges of the holes 108, the legs will compress radially to allow the DGF locking member 131 to be pulled completely through the holes 108. Once the locking member 131 has completely passed through the stent 100, the DGF locking member legs 132 can re-expand to full size to prevent backward motion of the DGF locking member 131 through the holes 108 in the atrial portion 104 of the stent and effectively lock the prosthetic hemi-valve 1 in the operative position.

In one aspect, referring to FIG. 11, the locking members 131 are configured to be selectively compressible from a cross-sectional profile larger than the diameter of the holes 108 in the atrial portion 104 of the stent to a cross-sectional profile smaller than the diameter of the holes 108 in the atrial portion 104 of the stent such that they can pass through the holes 108 in the atrial portion 104 of the stent, and then can be re-expanded to its original size to prevent the locking member 131 from passing through the holes 108 in the opposite direction. In this aspect, the locking member 131 can be configured with a conical, dome, arrow shaped or wedge structure with a plurality of slits using a rigid material, or optionally a deformable rubber-like cork or stopper structure with a cone, dome, wedge or spherical shape, or optionally clamp, clipping or snapping structure In an alternative aspect, the locking members 131 are configured to be selectively expandable from a cross-sectional profile smaller than the diameter of the holes 108 to a cross-sectional profile larger than the diameter of the holes 108 such that they can pass through the holes 108 in the atrial portion 104 of the stent and then can be selectively expanded such that they cannot pass through the holes 108 in the opposite direction. In this aspect, the locking member 131 can be formed, for instance, with a shape memory material and a mechanism to selectively hold the locking member 131 in a crimped state which can be selectively released to re-expand the locking member 131.

In one embodiment, also referring to FIG. 11, each of the locking members 131 include a conical shape with legs 132 that flare radially outwards. The legs 132 of the locking members 131 compress radially when passing through the hole 108 on the atrial portion 104 of the stent, and re-expand once it has passed fully through the hole 108 and lies on the top of the atrial portion 104 of the stent. The expanded legs 132 of the locking unit 131 prevent backward motion through the hole 108, thereby locking the prosthetic hemi-valve 1 into place.

It should be emphasized that the above-described aspects are merely possible examples of implementation, merely set forth a clear understanding of the principles of the present disclosure. Many variations and modifications can be made to the above-described embodiment(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims which follow, they are used only in a generic and descriptive sense, and not for the purposes of limiting the described invention, nor the claims which follow.

What is claimed is:

1. A prosthetic hemi-valve for replacing a native leaflet in a diseased heart valve, comprising:

a stent frame comprising an upper atrial portion configured to span at least a portion of a native annulus, a lower ventricular portion configured to span only a portion of the native annulus and allow for dynamic motion of at least one other native leaflet in an operative position, and a neck portion between the upper atrial portion and the lower ventricular portion, thereby defining a longitudinal axis therebetween;

a cushioning sealing ring attached to at least a portion of the stent frame;

a sealing skirt comprising an upper atrial portion and a lower ventricular portion attached to corresponding portions of the stent frame;

at least one dome-shaped prosthetic leaflet extending inward radially from an inner surface of the stent frame, wherein the at least one prosthetic leaflet is configured to be moveable from an open position to a closed position throughout the cardiac cycle in the operative position; and a plurality of dual-guiding-and-fixation members, each dual-guiding-and-fixation member comprising a portion configured to embed in the native tissue and a portion configured to selectively engage the stent frame to guide the stent frame to, and fix the stent frame relative to the native annulus, the operative position, wherein the upper atrial portion of the stent frame comprises a plurality of through-holes for receiving respective dual-guiding-and-fixation members therethrough, and wherein the dual-guiding-and-fixation members are configured to be fixated to the native annulus through the respective through-holes to fixate the upper atrial portion relative to the native annulus, and wherein the lower ventricular portion comprises a plurality of cells defining an axial height that varies around a circumference of the stent frame and wherein cells at lateral edges of the lower ventricular portion have an axial height that is shorter than cells at a middle portion of the stent frame between the lateral edges.

2. The prosthetic hemi-valve of claim 1, wherein the stent frame comprises a network of cells, or wires, configured to be radially collapsible and expandable.

3. The prosthetic hemi-valve of claim 2, wherein the upper atrial portion of the stent frame is configured with at least one row of cells, wherein the cells comprise struts that are oriented in a collapsible diamond-shaped structure that extend outward radially from the neck portion of the stent frame, wherein the diameter of the upper atrial portion is smallest near the neck portion and increases away from the neck portion.

4. The prosthetic hemi-valve of claim 3, wherein at least a portion of the struts towards a free upper-end of the upper atrial portion of the stent frame are configured to be curved or angled upward with an angle between 90° and 145° with respect to the rest of the upper atrial portion.

5. The prosthetic hemi-valve of claim 1, wherein each thorough hole has a diameter between about 0.5 and three millimeters (0.5-3 mm).

6. The prosthetic hemi-valve of claim 1, wherein the upper atrial portion of the stent frame comprises binding sites on opposing lateral edges of the stent frame that allow the opposing lateral edges to come together and engage each other during radial compression.

7. The prosthetic hemi-valve of claim 6, wherein the binding sites are configured with matching corresponding structures such that the binding sites fit together snugly and keep the stent frame in a substantially cylindrical configuration during crimping.

8. The prosthetic hemi-valve of claim 1, wherein the lower ventricular portion of the stent frame comprises a crescent shape with an anterior-posterior (AP) dimension ranging from about ten to forty millimeters (10-40 mm) and a commissure-to-commissure (CC) dimension ranging from about twenty to sixty millimeters (20-60 mm), and wherein the ventricular portion displaces at least one native leaflet in the operative position.

9. The prosthetic hemi-valve of claim 1, wherein the lower ventricular portion of the stent frame comprises free stent tips for attachment of prosthetic leaflet commissures.

10. The prosthetic hemi-valve of claim 1, wherein the lower ventricular portion of the stent frame comprises a hemi-conical shape defining a diameter that is smallest near the upper atrial portion and increases away from the upper atrial portion.

11. The prosthetic hemi-valve of claim 1, wherein the lower ventricular portion of the stent frame comprises one or more tabs extending from stent tips.

12. The prosthetic hemi-valve of claim 11, wherein the one or more tabs are configured for selective engagement to one or more portions of a delivery system.

13. The prosthetic hemi-valve of claim 1, wherein the lower ventricular portion of the stent frame defines an angle between about 65° and 120° with respect to the longitudinal axis and the upper atrial portion.

14. The prosthetic hemi-valve of claim 1, wherein the at least one dome-shaped prosthetic leaflet comprises a central domed leaflet, and two lateral domed leaflets that are smaller than the central domed leaflet.

15. The prosthetic hemi-valve of claim 1, wherein the sealing ring surrounds surfaces of the stent frame such that the sealing ring prevents the surrounded surfaces from coming into contact with the native tissue when the stent frame is positioned in the native annulus.

16. The prosthetic hemi-valve of claim 15, wherein the sealing ring surrounds at least the upper atrial portion of the stent frame.

17. The prosthetic hemi-valve of claim 15, wherein the sealing ring is attached to lateral edges of the stent frame such that the sealing ring surrounds the lateral edges.

18. A prosthetic valve for replacing a native leaflet in a diseased heart valve, comprising:

a stent frame comprising an upper end, a lower end, and lateral edges extending between the upper and lower ends and generally aligned along a longitudinal axis, the stent frame defining an arcuate cross-section between the upper and lower ends, the stent frame comprising an upper atrial portion, a lower ventricular portion configured to span only a portion of the native annulus and allow for motion of at least one native leaflet in an operative position, and a neck portion between the upper atrial portion and the lower ventricular portion;

a sealing skirt covering at least a portion of the stent frame; and at least one prosthetic leaflet extending radially inward from an inner surface of the stent frame, wherein the at least one prosthetic leaflet is configured to be moveable from an open position to a closed position to coapt with the at least one native leaflet throughout the cardiac cycle in the operative position, wherein the upper atrial portion comprises a plurality of through-holes for receiving respective dual-guiding-and-fixation members therethrough to fixate the upper atrial portion relative to the native annulus, and wherein the lower ventricular portion comprises a plurality of cells defining an axial height that varies around a circumference of the stent frame and wherein cells at the lateral edges of the lower ventricular portion have an axial height that is shorter than cells at a middle portion of the stent frame between the lateral edges.

19. A system for replacing a native leaflet in a diseased heart valve, comprising:

a prosthetic valve comprising:

a) a stent frame comprising an upper end, a lower end, and lateral edges extending between the upper and lower ends and generally aligned along a longitudinal axis, the stent frame defining an arcuate cross-section between the upper and lower ends, the stent frame comprising an upper atrial portion, a lower ventricular portion configured to span only a portion of the native annulus and allow for motion of at least one native leaflet in an operative position, and a neck portion between the upper atrial portion and the lower ventricular portion, wherein the upper atrial portion a plurality of through-holes;

b) a sealing skirt covering at least a portion of the stent frame;

c) at least one prosthetic leaflet extending radially inward from an inner surface of the stent frame, wherein the at least one prosthetic leaflet is configured to be moveable from an open position to a closed position to coapt with the at least one native leaflet throughout the cardiac cycle in the operative position, and a plurality of dual-guiding-and-fixation members configured to be received through respective through-holes of the plurality of through-holes and embed in the native tissue and engage the stent frame to fix the stent frame relative to the native annulus, wherein the lower ventricular portion comprises a plurality of cells defining an axial height that varies around a circumference of the stent frame and wherein cells at the lateral edges of the lower ventricular portion have an axial height that is shorter than cells at a middle portion of the stent frame.

* * * * *